United States Patent
Kusanagi et al.

(10) Patent No.: US 7,217,294 B2
(45) Date of Patent: *May 15, 2007

(54) ACELLULAR MATRIX IMPLANTS FOR TREATMENT OF ARTICULAR CARTILAGE, BONE OR OSTEOCHONDRAL DEFECTS AND INJURIES AND METHOD FOR USE THEREOF

(75) Inventors: Akihiko Kusanagi, Brookline, MA (US); Laurence J. B. Tarrant, Northampton, MA (US); Mary Beth Schmidt, Pomfret Center, CT (US)

(73) Assignee: Histogenics Corp., Northampton, MA (US)

( * ) Notice: Subject to any disclaimer, the term of this patent is extended or adjusted under 35 U.S.C. 154(b) by 104 days.

This patent is subject to a terminal disclaimer.

(21) Appl. No.: 10/882,581

(22) Filed: Jun. 30, 2004

(65) Prior Publication Data

US 2005/0043813 A1     Feb. 24, 2005

Related U.S. Application Data

(60) Provisional application No. 60/496,971, filed on Aug. 20, 2003.

(51) Int. Cl.
*A61F 2/30* (2006.01)
(52) U.S. Cl. .................... 623/18.11; 424/94.1; 424/484
(58) Field of Classification Search ............... 514/2, 514/21; 424/94.1, 484; 623/18.11
See application file for complete search history.

(56) References Cited

U.S. PATENT DOCUMENTS

| | | | |
|---|---|---|---|
| 5,306,311 A * | 4/1994 | Stone et al. ............. | 623/14.12 |
| 5,723,331 A | 3/1998 | Tubo et al. ............... | 435/366 |
| 5,786,217 A | 7/1998 | Tubo et al. ............... | 435/402 |
| 5,972,385 A * | 10/1999 | Liu et al. .................. | 424/400 |
| 6,150,163 A | 11/2000 | McPherson et al. ...... | 435/384 |
| 6,294,202 B1 | 9/2001 | Burns et al. .............. | 424/488 |
| 6,322,563 B1 | 11/2001 | Cummings et al. ....... | 606/72 |
| 6,352,558 B1 * | 3/2002 | Spector ................. | 623/18.11 |
| 6,440,427 B1 * | 8/2002 | Wadstrom ................ | 424/400 |
| 6,528,052 B1 * | 3/2003 | Smith et al. ............. | 424/93.7 |
| 2002/0082220 A1 | 6/2002 | Hoemann et al. .......... | 514/21 |

OTHER PUBLICATIONS

Robert C. Thomson, et al., Fabrication of Biodegradable Polymer Scaffolds to Engineer Trabecular Bone, *J. Biomater. Sci. Polymer Edn.*, 7/1:23-38, (1995).

* cited by examiner

*Primary Examiner*—Jean C. Witz
*Assistant Examiner*—Satyendra K. Singh
(74) *Attorney, Agent, or Firm*—Hana Verny; Peters, Verny, Jones, Schmitt & Aston, LLP

(57) ABSTRACT

An acellular matrix implant for treatment of defects and injuries of articular cartilage, bone or osteochondral bone and a method for treatment of injured, damaged, diseased or aged articular cartilage or bone, using the acellular matrix implant implanted into a joint cartilage lesion in situ and a bone-inducing composition implanted into an osteochondral or bone defect. A method for repair and restoration of the injured, damaged, diseased or aged cartilage or bone into its full functionality by implanting the acellular matrix implant between two layers of biologically acceptable sealants and/or the bone-inducing composition into the osteochondral bone or skeletal bone defect. A method for fabrication of the acellular matrix implant of the invention. A method for preparation of bone-inducing composition.

11 Claims, 12 Drawing Sheets

(7 of 12 Drawing Sheet(s) Filed in Color)

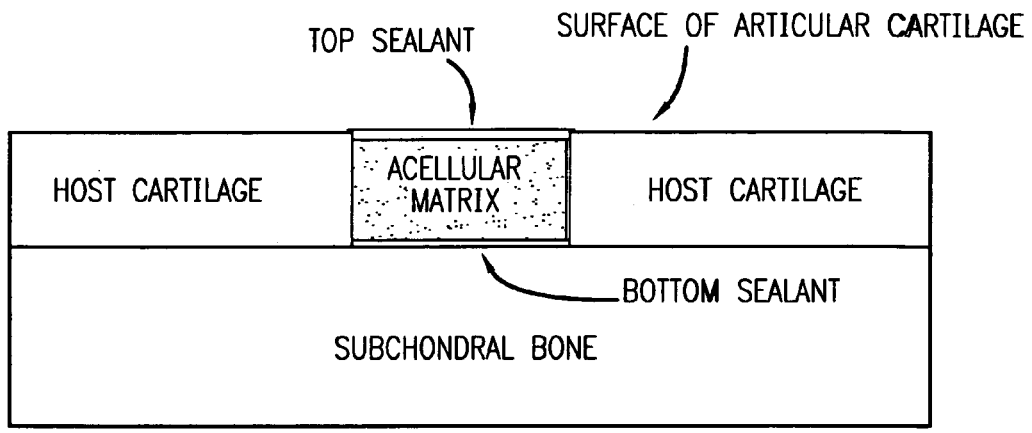
Schema of acellular matrix implantation in chondral defect
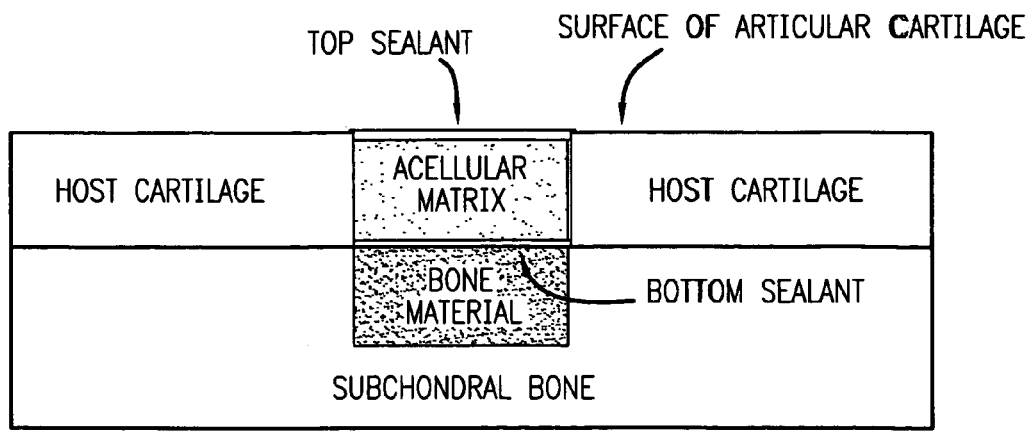
Schema of acellular matrix implantation in osteochondral defect Schema of acellular matrix implantation and defect creations
2 Defects (site A and B, size: 4mm in diameter, 1–1.5 mm in depth) were created in medial condyle (weight-bearing site) for acellular matrix implantation or control defect. The distance between site A and site B is approximately 4 mm.

image of acellular matrix
The size is 5 mm in diameter and 1.5 mm in thickness.

Longitudinal schema of honeycomb structure of acellular matrix
*: The pore size of each column is about 200–400 pm.

Gross anatomy of empty defect creation (control)
Size: 4 mm diameter; 1–1.5 mm depth Gross anatomy of acellular matrix implantation
Defect: 4 mm diameter; 1–1.5 mm depth
Acellular matrix: 5 mm diameter; 1.5 mm thickness
4 absorbable and 2 non-absorbable sutures
top and bottom sealant.

2 weeks after empty defect creation (control)

2 weeks after acellular matrix implantation

Empty defect control at site A (Safranin-O staining)
(29x magnification)
H: Surrounding host cartilage
D: Empty defect site
SB: Subchondral bone area Empty defect control at site A (Safranin-O staining)
(72x magnification)
F: Fibro-vascular pannus formation at empty defect site Empty defect control at site B (Safranin-O staining)
(29x magnification)
H: Surrounding host cartilage
D: Empty defect site
SB: Subchondral bone area Empty defect control at site B (Safranin-O staining)
(72x magnification)
F: Fibro-vascular pannus formation at empty defect site Acellular implantation at site A (Safranin-O staining)
(29x magnification)
H: Surrounding host cartilage
I: Implant site of acellular matrix
SB: Subchondral bone area Acellular implantation at site A (Safranin-O staining)
(72x magnification)
I: Implant site of acellular matrix

TRACE OF NON-ABSORBABLE SUTURE

SUPERFICIAL CARTILAGE LAYER

Acellular implantation at site B (Safranin-O staining)
(29x magnification)
H: Surrounding host cartilage
I: Implant site of acellular matrix
SB: Subchondral bone area

HIGHER MAGNIFICATION

Acellular implantation at site B (Safranin-O staining)
(72x magnification)
I: Implant site of acellular matrix Image of full thickness defect at femoral condyle of mini-pig
(72x magnification)
H: Surrounding host cartilage
D: Created full thickness defect after harvest
SB: Subchondral bone area

ACELLULAR MATRIX IMPLANTS FOR TREATMENT OF ARTICULAR CARTILAGE, BONE OR OSTEOCHONDRAL DEFECTS AND INJURIES AND METHOD FOR USE THEREOF

This application is based on and claims priority of the Provisional Application Ser. No. 60/496,971, filed Aug. 20, 2003, which is incorporated herein by reference.

BACKGROUND OF THE INVENTION

FIELD OF THE INVENTION

The current invention concerns acellular matrix implants and compositions for treatment of articular cartilage, bone or osteochondral defects and injuries and a method for treatment of such osteochondral defects and/or injured, damaged, diseased or aged articular cartilage or bone using an acellular matrix implant implanted into a joint cartilage lesion and/or into the osteochondral defect in situ wherein the osteochondral or bone defect is further implanted with a bone inducing composition or a carrier comprising said composition. The acellular matrix implant of the invention comprises a two or three dimensional biodegradable scaffold structure implanted into the joint cartilage lesion typically below or over one, two or several layers, or between two layers of biologically acceptable sealants. The implant and the method are particularly useful for repair and restoration of function of the injured or traumatized articular cartilage, bone or osteochondral defects of younger individuals. In particular, the invention concerns a method where the implantation of the acellular matrix implant of the invention initiates and achieves natural healing of the cartilage by activation and migration of chondrocytes from a native, surrounding cartilage into the cartilage defect and/or by inducing bone formation by depositing a bone inducing composition into the osteochondral and/or bone defect in conjunction with the acellular matrix implant or without the implant.

The method further concerns a formation of a new superficial cartilage layer overgrowing and sealing the lesion in the joint cartilage by applying a top sealant over the cartilage lesion as well as insulation of the lesion from the cell and blood debris, by applying a bottom sealant. Such formation of the superficial cartilage layer is also applicable to osteochondral cartilage and bone lesions where the bottom sealant is used for sealing and separating the cartilage and bone lesions and the top sealant is used to form the superficial cartilage layer.

The method for treatment of articular cartilage comprises preparation of the acellular implant, preparation of the lesion for implantation of said implant including a step of depositing a bottom sealant at the bottom of the cartilage lesion for sealing the joint cartilage lesion and protecting the implant from effects of blood-borne agents, implanting the implant of the invention into the lesion and depositing the top sealant over the implant. The method for treatment of osteochondral defects additionally typically comprises depositing a bone inducing composition or a carrier comprising said composition into the bone lesion wherein said bone lesion is covered by the bottom sealant thereby separating said bone and cartilage lesions. The method for treatment of bone defects comprises depositing the bone inducing composition or a carrier comprising said composition in a bone lesion which may optionally be lined with or covered with a bottom or top sealant.

The invention further concerns a method for repair and restoration of the injured, damaged, diseased or aged cartilage or bone into its full functionality and for treatment of injured cartilage by implanting the acellular matrix implant into the cartilage lesion between two or more layers of biologically acceptable sealants and/or depositing the bone inducing composition or a carrier comprising said composition into the bone lesion, covering said bone inducing composition or a carrier comprising said composition with the bottom sealant, depositing the acellular matrix implant into the cartilage lesion and covering said implant with the top sealant.

Additionally, the invention concerns a method for fabrication of an acellular implant of the invention for use in treatment of cartilage defects and for preparation of a bone inducing composition or a carrier comprising said composition for use in treatment of bone or osteochondral defects.

BACKGROUND AND RELATED DISCLOSURES

Damage to the articular cartilage which occurs in active individuals and older generation adults as a result of either acute or repetitive traumatic injury or aging is quite common. Such damaged cartilage leads to pain, affects mobility and results in debilitating disability.

Typical treatment choices, depending on lesion and symptom severity, are the rest and other conservative treatments, minor arthroscopic surgery to clean up and smooth the surface of the damaged cartilage area, and other surgical procedures such as microfracture, drilling, and abrasion. All of these may provide symptomatic relief, but the benefit is usually only temporary, especially if the person's pre-injury activity level is maintained. For example, severe and chronic forms of knee joint cartilage damage can lead to greater deterioration of the joint cartilage and may eventually lead to a total knee joint replacement. Nowadays, approximately 200,000 total knee replacement operations are performed annually. The artificial joint generally lasts only 10 to 15 years and the operation is, therefore, typically not recommended for people under the age of fifty.

Osteochondral diseases or injuries, which are a combination lesions of bone and cartilage, present yet another challenge for a treatment of which need is not being met by the currently available procedures and methods. For example, treatment of osteochondritis dissecans with autologous chondrocyte transplantation, described in *J. Bone and Joint Surgery*, 85A-Supplement 2: 17–24 (2003), requires multiple surgeries and at least three weeks for cell cultivation and growth.

It would, therefore, be extremely advantageous to have available a method for in situ treatment of these injuries which would effectively restore the cartilage or bone to its pre-injury state during one surgery and with minimal time needed for recovery, which treatment would be especially suitable for younger individuals who are more active and have better recovery capabilities.

Attempts to provide means and methods for repair of articular cartilage are disclosed, for example, in U.S. Pat. Nos. 5,723,331; 5,786,217; 6,150,163; 6,294,202; 6,322,563 and in the U.S. patent application Ser. No. 09/896,912, filed on Jun. 29, 2001.

U.S. Pat. No. 5,723,331 describes methods and compositions for preparation of synthetic cartilage for the repair of articular cartilage using ex vivo proliferated denuded chondrogenic cells seeded ex vivo, in the wells containing adhesive surface. These cells redifferentiate and begin to secrete cartilage-specific extracellular matrix thereby providing an unlimited amount of synthetic cartilage for surgical delivery to a site of the articular defect.

U.S. Pat. No. 5,786,217 describes methods for preparing a multi-cell layered synthetic cartilage patch prepared essentially by the same method as described in '331 patent except that the denuded cells are non-differentiated, and culturing these cells for a time necessary for these cells to differentiate and form a multicell layered synthetic cartilage.

U.S. application Ser. No. 09/896,912, filed on Jun. 29, 2001 concerns a method for repairing cartilage, meniscus, ligament, tendon, bone, skin, cornea, periodontal tissues, abscesses, resected tumors and ulcers by introducing into tissue a temperature dependent polymer gel in conjunction with at least one blood component which adheres to the tissue and promotes support for cell proliferation for repairing the tissue.

U.S. patent application Ser. Nos. 10/104,677; 10/625,822; 10/625,245 and 10/626,459 filed on Jul. 22, 2003, by inventors, hereby incorporated by reference, disclose neo-cartilage constructs subjected to an algorithm of certain specific conditions suitable for repair of injured or damaged articular cartilage.

None of the above cited references, however, results in repair and regeneration of cartilage or bone in situ without a need for several surgeries.

It is thus a primary objective of this invention to provide a method and a means for treatment of injured or traumatized cartilage, bone or cartilage-bone defects by depositing at least two separate layers of biologically acceptable adhesive sealants thereby forming a cavity in the injured lesion of the cartilage and implanting an acellular implant into said cavity between these two layers and, additionally, by providing a bone inducing composition or a carrier comprising said composition containing bone inducing agents and implanting said composition into the bone lesion of the osteochondral defects followed by the implantation of the acellular matrix implant into the cartilage defect. The method according to the invention results in induction of chondrocyte activation and migration from the surrounding native cartilage into the acellular implant's matrix and in the growth of the superficial cartilage layer over the implant thereby sealing the lesion and, when used for treatment of osteochondral defects, in migration of osteoblast into the bone lesion and in healing of the bone defect as well as defect of the articular cartilage.

All patents, patent applications and publications cited herein are hereby incorporated by reference.

SUMMARY

One aspect of the current invention is an acellular matrix implant for treatment of defects and injuries of articular cartilage.

Another aspect of the current invention is an acellular matrix implant in combination with a bone inducing composition or a carrier comprising said composition for treatment of osteochondral defects and injuries.

Still another aspect of the current invention is an acellular bone implant comprising a bone inducing composition or a carrier comprising said composition for implantation into a bone lesion for treatment of bone defects and injuries.

Yet another aspect of the current invention is a method for fabrication of an acellular matrix implant of the invention.

Still another aspect of the current invention is a method for preparation of an acellular matrix implant wherein said matrix is a sponge, honeycomb, scaffold, thermo-reversible gelation hydrogel (TRGH) or a polymer of an aromatic organic acid.

Yet another aspect of the current invention is a method for treatment of injured, damaged, diseased or aged articular cartilage using the acellular matrix implant implanted into a joint cartilage lesion in situ.

Still yet another aspect of the current invention is an acellular matrix implant used in a method where the implantation of the acellular matrix implant of the invention initiates and achieves activation and induction of migration of chondrocytes from a native surrounding cartilage into the acellular matrix implant deposited within a cartilage defect.

Still yet another aspect of the current invention is a method for treatment of osteochondral defects by implanting an acellular matrix implant into the cartilage lesion in conjunction with depositing a bone inducing composition or a carrier comprising said composition into an osteochondral lesion in situ.

Still another aspect of the current invention is a bone inducing composition or a carrier comprising said composition containing bone inducing agents such as a demineralized bone powder, calcium phosphate, hydroxyapatite, organoapatite, titanium oxide, poly-L-lactic or polyglycolic acid or a copolymer thereof or a bone morphogenic protein used in a method where the deposition of said composition into the bone lesion initiates migration of osteoblast and achieves natural healing of the underlying bone.

Still yet another aspect of the current invention is a bone inducing composition or a carrier comprising said composition deposited into a bone lesion of the osteochondral defect in conjunction with implantation of an acellular matrix implant into the cartilage lesion useful for treatment of osteochondral defects.

Still yet another aspect of the current invention is a method for treatment of bone lesions caused by bone injuries or defects said treatment accomplished by implanting a bone inducing composition or a carrier comprising said composition into the bone lesion in situ.

Still another aspect of the current invention is a bone inducing composition or a carrier comprising said composition containing bone inducing agents such as a demineralized bone powder, calcium phosphate, hydroxyapatite, organoapatite, titanium oxide, poly-L-lactic or polyglycolic acid or a copolymer thereof or a bone morphogenic protein alone, in combination, or incorporated into a carrier, such as a matrix, hydrogel, sponge, honeycomb, scaffold or a polymer of an aromatic organic acid, used in a method where the deposition of said composition into the bone lesion initiates migration of osteoblast and achieves natural healing of the underlying bone.

Still yet another aspect of the current invention is a bone inducing composition or a carrier comprising said composition deposited into a bone lesion for treatment of a bone defect alone or, where appropriate, in conjunction with implantation of an acellular matrix implant into the cartilage lesion or osteochondral implant useful for treatment of osteochondral defects.

Yet another aspect of the current invention is a method for treatment of injured, damaged, diseased or aged articular cartilage using an acellular matrix implant implanted into a joint cartilage lesion in situ, said method further comprising a formation of a new superficial cartilage layer overgrowing and sealing the lesion in the joint articular cartilage by applying a top sealant over the lesion and further applying a bottom sealant over the bottom of the lesion, said bottom sealant providing protection of the lesion against a cell and blood debris migration.

Another aspect of the current invention is a method for treatment of osteochondral defects by depositing a bone inducing composition or a carrier comprising said composition comprising bone inducing agents into a bone lesion, depositing a bottom sealant over the bone inducing composition or a carrier comprising said composition, implanting an acellular matrix implant into the articular lesion and depositing a top sealant over the acellular matrix implant.

Still another aspect of the current invention is an acellular matrix implant for use in treatments of the cartilage or bone lesions comprising a two or three dimensional biodegradable sponge, honeycomb, hydrogel, scaffold or a polymer of an aromatic organic acid matrix implanted into the joint cartilage lesion between two layers, top and bottom, of biologically acceptable sealants.

Still yet another aspect of the current invention is a method for treatment of articular cartilage injury comprising steps:

a) preparation of an acellular matrix implant;

b) preparation of a cartilage lesion for implantation of said implant, including a step of depositing a bottom sealant at the bottom of the cartilage lesion for sealing of said lesion and protecting the implant from migration of blood-borne agents;

c) implanting the implant into the lesion; and d) depositing a top sealant over the acellular matrix implant.

Still yet another aspect of the current invention is a method for repair and restoration of damaged, injured, diseased or aged cartilage to a functional cartilage, said method comprising steps:

a) preparing an acellular matrix implant as a collagenous sponge, collagenous porous scaffold or honeycomb, thermo-reversible gelation hydrogel (TRGH) or a polymer of an aromatic organic acid matrix, wherein said sponge, scaffold, polymer of the aromatic organic acid or TRGH are biodegradable, will disintegrate with time and be metabolically removed from the healed lesion and replaced with a hyaline cartilage, said matrix optionally comprising matrix remodeling enzymes, such as matrix metalloproteinases, aggrecanases, cathepsins and/or other biologically active components;

b) introducing a layer of a biologically acceptable bottom sealant into a cartilage lesion;

c) implanting said implant into said lesion into a cavity formed by the bottom layer of said bottom sealant; and d) introducing a top layer of a second biologically acceptable top sealant over said implant wherein said top sealant may or may not be the same as the bottom sealant and wherein a combination of said implant and said top sealant results in formation and growth of a superficial cartilage layer sealing the cartilage lesion in situ.

Still another aspect of the current invention is an acellular matrix implant comprising a thermo-reversible gelation hydrogel (TRGH) deposited into a lesion cavity formed above the bottom sealant layer, or into the cavity between the top and bottom sealant, said TRGH deposited into said cavity either incorporated into a collagenous sponge or scaffold or as a sol at temperatures between about 5 to about 30° C., wherein within said cavity and at the body temperature said TRGH converts from the fluidic sol into a solid gel and in this form, its presence provides a structural support for migration of chondrocytes from a surrounding native cartilage and formation of extracellular matrix, wherein said TRGH is biodegradable, will disintegrate with time and be metabolically removed from the lesion and replaced with a hyaline cartilage.

Still yet another aspect of the current invention is a method for treatment of osteochondral defects, said method comprising steps:

a) preparing a bone inducing composition or a carrier comprising said composition comprising one or several bone inducing agents for implantation into a bone lesion;

b) preparing an acellular matrix implant for implantation into a cartilage lesion as a collagenous sponge, collagenous porous scaffold or honeycomb or thermo-reversible gelation hydrogel (TRGH) matrix support wherein said sponge, scaffold or TRGH are biodegradable, will disintegrate with time and be metabolically removed from the lesion and replaced with a hyaline cartilage, said matrix optionally comprising matrix remodeling enzymes, matrix metalloproteinases, aggrecanases and cathepsins;

c) introducing said bone inducing composition or a carrier comprising said composition into a bone lesion;

d) covering said bone inducing composition or a carrier comprising said composition with a bottom sealant;

e) implanting said acellular matrix implant into said cartilage lesion over the bottom sealant; and f) introducing a layer of a top sealant over said implant wherein said top and bottom sealants may or may not be the same and wherein a combination of said acellular matrix implant and said top sealant results in formation and growth of a superficial cartilage layer sealing the cartilage lesion in situ.

Still yet another aspect of the current invention is a bone inducing composition or a carrier comprising said composition comprising bone inducing agents for treatment of osteochondral defects further in combination with an acellular matrix implant comprising a thermo-reversible gelation hydrogel (TRGH) each deposited separately into a bone or cartilage lesion, wherein said composition provides a means for rebuilding the bone and migration of osteoblast into the bone lesion and wherein said implant provides a structural support for migration of chondrocytes from a surrounding native cartilage and formation of extracellular matrix.

BRIEF DESCRIPTION OF DRAWINGS

The file of this patent contains at least one drawing executed in color. Copies of this patent with color drawing(s) will be provided by the Patent and Trademark Office upon request and payment of necessary fee.

FIG. 1A is an enlarged schematic representation of the cartilage lesion within the host cartilage with underlaying uninjured bone, showing a bottom sealant deposited at the bottom of the lesion, an acellular matrix implant deposited over the bottom sealant and covered with a top sealant. FIG. 1B is an enlarged schematic representation of the osteochondral defect showing the articular lesion, bone lesion, emplacement of the bone inducing composition (bone material) or a carrier comprising said composition into the bone lesion, emplacement of top and bottom sealants and emplacement of the acellular matrix implant.

FIG. 12 illustrates a degradation pattern in vivo of the top sealant 3 months after the acellular matrix implantation. The formed superficial cartilage layer was formed over the implant and the sealant was partially degraded at three months after the implantation.

DEFINITIONS

Figure 1C:
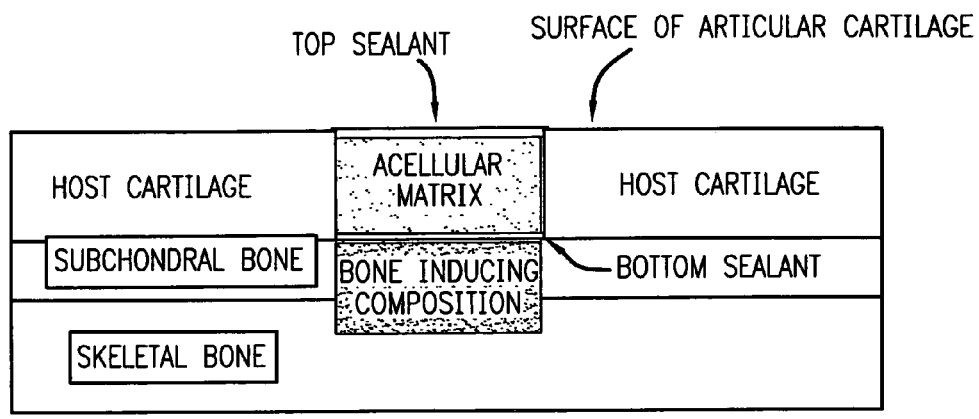
FIG. 1C is an enlarged schematic representation of the bone defect showing the articular lesion, and combined osteochondral and skeletal bone lesion, emplacement of the bone inducing composition or a carrier comprising said composition into the bone and osteochondral lesion, emplacement of top and bottom sealants and emplacement of the acellular matrix implant.

As used herein:

"Acellular" means an implant lacking any biologically active cells.

"Acellular matrix implant" or "acellular implant" means a biologically acceptable collagenous implant whether in the form of collagenous sponge, collagenous honeycomb, collagenous scaffold or thermo-reversible gelation hydrogel without any biologically active cells, forming a matrix into which the chondrocytes may migrate.

"Articular cartilage" means a hyaline cartilage of the joints, such as the knee joint.

"Subchondral" means a structure underlying a joint cartilage.

"Subchondral bone" means a bone of specific composition, typically very dense, but thin layer of bone just below the zone of calcified cartilage and above the cancellous or trabecular bone that forms the bulk of the bone structure of the limb.

"Osteochondral" means combined area of the cartilage and bone where a lesion or lesions occur.

"Osteochondral defect" means a lesion which is a composite lesion of cartilage and underlying bone.

"Bone defect" or "bone lesion" means the defect which is localized under the subchondral bone region and is thus a defect/lesion in a skeletal bone.

"Osteoblast" means a bone forming cell.

"Chondrocyte" means a nondividing cartilage cell which occupies a lacuna within the cartilage matrix.

"Support matrix" means biologically acceptable sol-gel or collagenous sponge, scaffold, honeycomb, hydrogel or a polymer of an aromatic organic acid suitable for receiving activated migrating chondrocytes or osteocytes that provides a structural support for growth and three-dimensional propagation of chondrocytes and for formulating of new hyaline cartilage or for migration of osteochondrocytes into the bone lesions. The support matrix is prepared from such materials as Type I collagen, Type II collagen, Type IV collagen, gelatin, agarose, cell-contracted collagen containing proteoglycans, glycosaminoglycans or glycoproteins, polymers of aromatic organic acids, fibronectin, laminin, bioactive peptide growth factors, cytokines, elastin, fibrin, synthetic polymeric fibers made of poly-acids such as polylactic, polyglycolic or polyamino acids, polycaprolactones, polyamino acids, polypeptide gel, copolymers thereof and combinations thereof. The gel solution matrix-may be a polymeric thermo-reversible gelling hydrogel. The support matrix is preferably biocompatible, biodegradable, hydrophilic, non-reactive, has a neutral charge and is able to have or has a defined structure.

"Mature hyaline cartilage" means cartilage consisting of groups of isogenous chondrocytes located within lacunae cavities which are scattered throughout an extracellular collagen matrix.

"Sealant" means a biologically acceptable typically rapidly gelling formulation having a specified range of adhesive and cohesive properties. Sealant is thus a biologically acceptable rapidly gelling synthetic compound having adhesive and/or gluing properties, and is typically a hydrogel, such as derivatized polyethylene glycol (PEG), or a protein, such as albumin, which is preferably cross-linked with a collagen compound. The sealant of the invention typically gels and/or bonds rapidly upon contact with tissue, particularly with tissue containing collagen.

"Modified sealant" means any suitable sealant for use in the invention which has a polymerization time of at least 30 seconds.

"Bone-inducing composition" or "a carrier comprising said composition" means a composition comprising at least one bone-inducing agent or, preferably, a combination of several agents, typically dissolved in a carrier or incorporated into a matrix similar to the acellular matrix implant.

"Bone-inducing carrier", "carrier comprising bone-inducing composition" or "bone acellular implant" means any carrier which contains bone-inducing agents and which by itself promotes bone formation or is suitable for depositing said bone-inducing composition comprising at least one bone-inducing agent or, preferably, a combination of several agents. Typically, the carrier will be an acellular biodegradable porous matrix, hydrogel, sponge, honeycomb, scaffold or a polymer of an aromatic organic acid structure having large pores from about 50 to about 150 μm, which pores encourage migration of osteoblast and interconnecting small pores of about 0.1 to about 10 μm which promote support and encourage formation of bone. The surface of such carrier might be negatively charged encouraging pseudopod attachment of osteoblasts and subsequent bone formation. One example of the suitable carrier promoting bone formation is a polymer of an aromatic organic acid with controllable degree of degradation which is sufficiently hard but has a spongiform structure.

"Bone-inducing agents" means agents which induce, support or promote bone growth and repair of bone defects. Exemplary bone-inducing agents are calcium phosphate, hydroxyapatite, organoapatite, titanium oxide, demineralized bone powder, poly-L-lactic and polyglycolic acid or a copolymer thereof or a bone morphogenic protein, among others.

"Bottom sealant" or "first sealant" means a biologically acceptable tissue sealant which is deposited at the bottom of the lesion. In case of the osteochondral defect, the first sealant is deposited over the bone-inducing composition or a carrier comprising said composition deposited into the bone lesion effectively sealing, separating and protecting the bone lesion from chondrocyte migration as well as protecting the cartilage lesion from migration of osteocytes.

"Top sealant" or "second sealant" means a biologically acceptable sealant which is deposited above and over the acellular matrix implant implanted into a lesion and may promote formation of the superficial cartilage layer. The second (top) sealant may or may not be the same as the first (bottom) sealant and is preferably a cross-linked polyethylene glycol hydrogel with methyl-collagen.

"De novo" or "de novo formation" means the new production of cells, such as chondrocytes, fibroblasts, fibrochondrocytes, tenocytes, osteoblasts and stem cells capable of differentiation, or tissues such as cartilage connective tissue, hyaline cartilage, fibrocartilage, tendon, and bone within a support structure, such as multi-layered system, scaffold or collagen matrix or formation of superficial cartilage layer.

"Superficial cartilage layer" means an outermost layer of cartilage that forms the layer of squamous-like flattened superficial zone chondrocytes covering the layer of the second sealant and overgrowing the lesion.

"Thermo-reversible" means a compound or composition changing its physical properties such as viscosity and consistency, from sol to gel, depending on the temperature. The thermo-reversible composition is typically completely in a sol (liquid) state at between about 5 and 15° C. and in a gel (solid) state at about 25–30° C. and above. The gel/sol state in between shows a lesser or higher degree of viscosity and depends on the temperature. When the temperature is higher than 15° C., the sol begins to change into gel and with the temperature closer to 30–37° the sol becomes more and more solidified as gel. At lower temperatures, typically lower than 15° C., the sol has more liquid consistency.

"TRGH" means thermo-reversible gelation hydrogel material in which the sol-gel transition occurs on the opposite temperature cycle of agar and gelatin gels. Consequently, the viscous fluidic phase is in a sol stage and the solid phase is in a gel stage. TRGH has very quick sol-gel transformation which requires no cure time and occurs simply as a function of temperature without hysteresis. The sol-gel transition temperature can be set at any temperature in the range from 5° C. to 70° C. by molecular design of thermo-reversible gelation polymer (TGP), a high molecular weight polymer of which less than 5 wt % is enough for hydrogel formation.

"Sol-gel solution" means a colloidal suspension which, under certain conditions, transitions from a liquid (sol) to a solid material (gel). The "sol" is a suspension of aqueous collagen that is transitioned, by heat treatment, into a gel.

"GAG" means glycosaminoglycan.

"S-GAG" means sulfated glycosaminoglycan.

"Aggrecanase" means aggrecanase enzyme.

"Cathepsin" means a proteinase or peptidase enzyme.

"MMP" means matrix metalloproteinase, an enzyme associated with cartilage degeneration in an injured or diseased joint.

"DMB" means dimethylene blue used for staining of chondrocytes.

"Superficial zone cartilage" means the flattened outermost layer of chondrocytes covering the extracellular matrix intermediate zone and deeper zone of mature articular cartilage in which non-dividing cells are dispersed.

"Connective tissue" means tissue that protect and support the body organs, and also tissues that hold organs together. Examples of such tissues include mesenchyme, mucous, connective, reticular, elastic, collagenous, bone, blood, or cartilage tissue such as hyaline cartilage, fibrocartilage, and elastic cartilage.

"Adhesive strength" means a peel bond strength measurement, which can be accomplished by bonding two plastic tabs with an adhesive formulation. The tabs can be formed by cutting 1×5 cm strips from polystyrene weighing boats. To the surface of the boat are bonded (using commercial cyanoacrylate Superglue), sheets of sausage casing (collagen sheeting, available from butcher supply houses). The sausage casing is hydrated in water or physiological saline for 20 min to one hour and the adhesive is applied to a 1×1 cm area at one end of the tab; the adhesive is cured. Then, the free ends of the tab are each bent and attached to the upper and lower grips, respectively, of a tensile testing apparatus and pulled at 10 mm/min strain rate, recording the force in Newtons to peel. A constant force trace allows estimation of N/m, or force per width of the strip. A minimum force per width of 10 N/m is desired; 100 N/m or higher is more desirable. Alternatively, the same tab can be bonded (a single tab) over a 1×1 cm area to tissue, either dissected or exposed tissue in a living animal, during surgery. The free end of the tab is then gripped or attached through a perforation to a hook affixed to a hand-held tensile test device (Omega DFG51-2 digital force gauge; Omega Engineering, Stanford, Conn.) and pulled upward at approximately 1 cm/sec. The maximum force required to detach the tab from the tissue is recorded. The minimum force desired in such measurements would be 0.1 N to detach the tab. Forces or 0.2 to 1 N are more desirable.

"Cohesive strength" means the force required to achieve tensile failure and is measured using a tensile test apparatus. The glue or adhesive can be cured in a "dog-bone"-shaped mold. The wide ends of the formed solid adhesive can then be affixed, using cyanoacrylate (Superglue) to plastic tabs, and gripped in the test apparatus. Force at extensional failure should be at least 0.2 MPa (2 N/cm$^2$) but preferably 0.8 to 1 MPa or higher.

"Lap shear measurements" means a test of bonding strength, in which the sealant formulation is applied to overlapping tabs of tissue, cured, and then the force to pull the tabs apart is measured. The test reflects adhesive and cohesive bonding; strong adhesives will exhibit values of 0.5 up to 4–6 N/cm$^2$ of overlap area.

DETAILED DESCRIPTION OF THE INVENTION

This invention is based on findings that when a biodegradable acellular matrix implant, such as a collagenous sponge matrix, collagenous scaffold matrix or thermo-reversible gelation hydrogel matrix implant, is deposited into a lesion of injured, traumatized, aged or diseased cartilage or, in conjunction with a bone-inducing composition or a carrier comprising said composition comprising bone activating agents, into an osteochondral or bone defect, within time, this acellular matrix implant activates mature but non-dividing chondrocytes present in the surrounding native cartilage, induces them to migrate to a site of the articular cartilage defect and generates a new extracellular matrix ultimately resulting in formation of a healthy hyaline cartilage and/or, in case of the bone or osteochondral defect, it induces migration of osteoblast cells from surrounding healthy bone or subchondral bone. Under these circumstances, the second, top sealant deposited over the acellular matrix implant will promote in situ formation of superficial cartilage layer over the cartilage lesion containing the implant. Such superficial cartilage layer will be also generated when the top sealant is deposited over the osteochondral defect, which, additionally, will comprise depositing of the bone-inducing composition or a carrier comprising said composition into the bone lesion and covering said composition with a first, bottom sealant.

The invention thus, in its broadest scope, concerns a method for repair and restoration of damaged, injured, traumatized or aged cartilage or for repair of bone or osteochondral defects and restoration of both the cartilage and/or bone into their full functionality by implanting, during arthroscopic surgery, an acellular matrix implant and/or depositing a bone-inducing composition or a carrier comprising said composition into the bone lesion before implanting the acellular matrix implant into the cartilage lesion. The invention further includes a method for fabrication of said acellular matrix implant, preparation of said bone-inducing composition or a carrier comprising said composition and a method for de novo formation of a superficial cartilage layer in situ.

Briefly, for treatment of the articular lesions, the invention comprises preparation of the acellular matrix implant for implanting into a joint cartilage lesion, said implant comprising a collagenous, thermo-reversible gel or an aromatic organic acid polymer support matrix in two or three-dimensions. The acellular matrix implant may contain various supplements, such as matrix remodeling enzymes, metalloproteinases (MMP-9, MMP-2, MMP-3), aggrecanases, cathepsins, growth factors, donor's serum, ascorbic acid, insulin-transferrin-sodium (ITS), etc., in concentrations which are known in the art to induce growth, differentiation and phenotype stability.

For treatment of osteochondral defects, the invention comprises preparation of a bone-inducing composition or a carrier comprising said composition comprised of bone-inducing agents, such as demineralized bone powder, calcium phosphate, hydroxyapatite, organoapatite, titanium oxide, poly-L-lactic and polyglycolic acid or a copolymer thereof, alone or in combination, or a bone morphogenic protein, depositing said composition into the bone lesion and covering said bone-inducing composition or a carrier comprising said composition with the first bottom sealant followed by depositing said acellular matrix implant into the cartilage lesion and covering said implant with the second, top sealant.

For treatment of bone defects, the invention comprises preparation of a bone-inducing composition or a carrier comprising said composition comprised of bone-inducing agents, such as demineralized bone powder, calcium phosphate, hydroxyapatite, organoapatite, titanium oxide, poly-L-lactic and polyglycolic acid or a copolymer thereof, alone or in combination, or a bone morphogenic protein in amounts needed to fill the bone lesion, and depositing said composition into the bone lesion. Said lesion may optionally be covered with the bottom or top sealant. Typically, the bottom sealant is not deposited at the bottom of the bone lesion but if needed, it can be.

The acellular matrix implant is implanted into a cartilage lesion cavity formed by at least two layers of adhesive sealants. However, in certain circumstances, the acellular matrix implant may be also deposited into the cartilage lesion without either the bottom or top sealant or without both sealants.

When the sealants are used in the method for repair of cartilage, the first (bottom) layer of the sealant is deposited at and covers the bottom of the cartilage lesion. Its function is to protect the integrity of said lesion from cell migration and from effects of various blood and tissue debris and metabolites and also to form a bottom of the cavity into which the acellular matrix implant is deposited. The first layer of the sealant may also become a covering layer deposited over the bone-inducing composition or a carrier comprising said composition placed into the bone lesion within the subchondral bone or bone area.

Studies of induced defects of the pig's femoral condyle confirmed that implantation of a biodegradable acellular matrix implant combined with a implantation procedure disclosed herein and performed under defined conditions induces activation and promotes chondrocyte migration from surrounding native host cartilage resulting in formation of extracellular matrix (ECM) of a regenerated hyaline-like cartilage within the lesion at the injured site. Similarly, a deposition of a bone-inducing composition or a carrier comprising said composition comprising bone-inducing agents into the bone defect promotes natural healing of bone by inducing migration of osteoblast into said bone lesion and, combined with the acellular matrix implant as described above, leads to healing and reconstruction of both the bone and cartilage.

The method for using the acellular matrix implant for generation of the hyaline cartilage is particularly suitable for treatment of lesions in younger patients with focused lesions where the cartilage has not developed an incipient osteoarthritic conditions, that is in patients who would typically be treated with microfracture or with cleaning the articular cartilage in the joint, such as in, for example, arthroscopic surgery following a sports injury. Such patients stand a high probability of restoring a fully functional hyaline cartilage, or in case of osteochondral defects, a fully functional cartilage and bone, without need of and aggravation associated with undergoing additional one or multiple surgeries.

One advantage of using the above-described method is that the acellular matrix implant and/or the bone-inducing composition or a carrier comprising such composition is non-immunogenic, can be pre-manufactured well before the operation and can be introduced during the first arthroscopy, when the diagnosis, cleaning and debridement of the lesion takes place without a need for further biopsy, cell culturing, additional surgeries or treatments to prevent immune reactions.

I. Cartilage, Bone and Properties Thereof

Cartilage and bone, both, are connective tissues providing support in the body for other soft tissues.

Bone is a hard connective tissue forming a skeleton, consisting of osteoblast cells embedded in a matrix of mineralized ground substance and collagen fibers. The collagen fibers are impregnated with a form of calcium phosphate similar to hydroxyapatite as well as with substantial quantities of carbonate, citrate, sodium and magnesium. Bone is composed of approximately 75% of inorganic material and 25% of organic material. Bone consists of a dense outer layer of compact substance covered by periosteum and an inner, loose spongy substance, i.e. bone marrow. Bone emplaced immediately below the cartilage is called subchondral bone and it is a bone of specific composition and structure that is itself underlain by the cancellous bone of the limb.

Cartilage is a mature connective tissue covering joints and bones which is comprised of metabolically active but non-dividing chondrocytes. This results in essential non-existence of spontaneous ability of the cartilage to self-repair following the injury or damage caused by age or disease.

Cartilage is characterized by its poor vascularity and a firm consistency, and consists of mature non-dividing chondrocytes (cells), collagen (interstitial matrix of fibers) and a ground proteoglycan substance (glycoaminoglycans or mucopolysaccharides). Later two are cumulatively known as extracellular matrix.

There are three kinds of cartilage, namely hyaline cartilage, elastic cartilage and fibrocartilage. Hyaline cartilage, found primarily in joints, has a frosted glass appearance with interstitial substance containing fine type II collagen fibers obscured by proteoglycan. Elastic cartilage is a cartilage in which, in addition to the collagen fibers and proteoglycan, the cells are surrounded by a capsular matrix further surrounded by an interstitial matrix containing elastic fiber network. The elastic cartilage is found, for example, in the central portion of the epiglottis. Fibrocartilage contains Type I collagen fibers and is typically found in transitional tissues between tendons, ligaments or bones and also as a low quality replacement of injured hyaline cartilage. This invention utilizes properties of acellular matrix implant combined with certain conditions existing naturally in the surrounding native cartilage further combined with certain steps according to the method of the invention, to achieve the healing and replacement of injured cartilage with the healthy and functional hyaline cartilage.

A. Articular Cartilage and Articular Cartilage Defects

The articular cartilage of the joints, such as the knee cartilage, is hyaline cartilage which consists of approximately 5% of chondrocytes (total volume) seeded in approximately 95% extracellular matrix (total volume). The extracellular matrix contains a variety of macromolecules, including collagen and glycosaminoglycan (GAG). The structure of the hyaline cartilage matrix allows it to reasonably well absorb shock and withstand shearing and compression forces. Normal hyaline cartilage has also an extremely low coefficient of friction at the articular surface.

Healthy hyaline cartilage has a contiguous consistency without any lesions, tears, cracks, ruptures, holes or shredded surface. Due to trauma, injury, disease such as osteoarthritis, or aging, however, the contiguous surface of the cartilage is disturbed and the cartilage surface shows cracks, tears, ruptures, holes or shredded surface resulting in cartilage lesions.

The articular cartilage is an unique tissue with no vascular, nerve, or lymphatic supply. The lack of vascular and lymphatic circulation may be one of the reasons why articular cartilage has such a poor, almost non-existent intrinsic capacity to heal. The mature metabolically active but non-dividing chondrocytes in their lacunae surrounded by extracellular matrix do not respond to damage signals by generating high-quality hyaline cartilage. After a significant injury, unique mechanical functions of articular cartilage are never reestablished spontaneously and never completely because the water-absorption capacity of the type II collagen/proteoglycan network is disturbed. The usual replacement material for hyaline cartilage, which might develop spontaneously in response to the injury of hyaline cartilage and which replaces the injured cartilage, is the much weaker and functionally inferior fibrocartilage.

Defects occurring due to cartilage trauma, injury, disease or aging are tears, cracks, ruptures or holes which are solely located in the joint cartilage. According to the method of the invention, when such defect is treated, the implant is deposited within the lesion, as illustrated in FIG. 1A.

FIG. 1A is a schematic representation of an acellular matrix implant implantation into the cartilage defect. The scheme shows the lesion implantation site with acellular matrix implanted therein surrounded by host cartilage with underlaying undisturbed subchondral bone. Emplacement of the top and bottom sealants are also illustrated.

B. Currently Available Procedures for Repair of Cartilage

A variety of surgical procedures have been developed and used in attempts to repair damaged cartilage. These procedures are performed with the intent of allowing bone marrow cells to infiltrate the defect and promote its healing. Generally, these procedures are only partly, if at all, successful. More often than not, these procedures result in formation of a fibrous cartilage tissue (fibrocartilage) which does fill and repair the cartilage lesion but, because it is qualitatively different being made of Type I collagen fibers, it is less durable, less resilient and generally inferior than the normal articular hyaline cartilage and thus has only a limited ability to withstand shock and shearing forces than does healthy hyaline cartilage. Since all diarthroid joints, particularly knees joints, are constantly subjected to relatively large loads and shearing forces, replacement of the healthy hyaline cartilage with fibrocartilage does not result in complete tissue repair and functional recovery.

Among the currently available procedures for repair of the articular cartilage injuries are the microfracture technique, the mosaicplasty technique and autologous chondrocyte implantation (ACI). However, in one way or another, all these techniques are problematic. The mosaicplasty technique and ACI, for example, need a biopsy of cartilage from a non-damaged articular cartilage area and subsequent cell culture to grow the number of cells. As a consequence, these techniques require at least two separate surgeries. One system, the Carticel® system additionally requires a second surgery site to harvest portion of and, therefore, disrupt the tibial periosteum. While the microfracture technique does not require a biopsy of articular cartilage, the resulting tissue which develops is always fibrocartilage.

The method for treatment of injured, traumatized, diseased or aged cartilage according to the current invention obviates the above problems as it comprises treating the injured, traumatized, diseased or aged cartilage with an acellular matrix implant without need to remove tissue or cells for culturing, said implant prepared by methods described below and implanted into the cartilage lesion during the debriding surgery, as described below.

C. Osteochondral Area and Osteochondral Defects

Osteochondral area, in this context, means an area where the bone and cartilage connect to each other and where the osteochondral defects often develop following the injury.

FIG. 1B is a schematic representation of implantation of an acellular matrix implant in the osteochondral defect. The scheme shows the cartilage lesion implantation site with the acellular matrix implanted therein surrounded by host cartilage with underlaying bone lesion in the subchondral bone. A bone-inducing composition or an acellular implant carrier comprising said composition is deposited into the bone lesion separated from the cartilage lesion by the bottom sealant. Emplacement of the top and bottom sealants illustrates separation of the bone lesion from the cartilage lesion by the bottom sealant such that each the cartilage lesion and the bone lesion are treated separately using different means, namely the acellular matrix implant for treatment of the cartilage lesion and the bone-inducing composition or the acellular carrier comprising said composition for treatment of the bone defect.

Osteochondral defects are thus defects that are composites of cartilage and underlying bone. Up-to-date, commonly used treatments for osteochondral defects are surgical excisions, mosaicplasty, osteochondral autogenous grafting, allogenic grafting, bone cementing, deposition of metal or ceramic solid composite materials, porous biomaterials and, lately, a transplantation of autologous chondrocytes. Regretfully, none of these procedures was found to be successful in treating these defects and safe or comfortable for a patient. Typically, these procedures involve two or more surgical procedures and long period, generally at least two to three weeks, of time to culture the transplantable cells. For example, mosaicplasty requires removal of circular pieces of healthy subchondral bone and cartilage to be used as transplantable plugs at a defect site. One obvious problem with mosaicplasty is that the surgeon, in an open surgery, is disrupting healthy tissue in order to repair the subchondral defect. Clearly, the multiple surgeries and long period of time between them necessarily extend a time of recovery to fully functional joint and often result only in partial functional restoration as both the bone and cartilage defects are filled with the fibrocartilage instead of the bone and hyaline cartilage.

One example of the osteochondral defect which is common and very difficult to treat is osteochodritis dissecans. Osteochodritis dissecans is a focal bone-cartilage lesion characterized by separation of an osteochondral fragment from the articular surface. Attempts to treat this injury with allograph transplants faces the same problem of second surgery and disruption of the healthy tissue, as described above. Thus it would be advantageous to have available a method which would remove a need for second surgery and yet provide a means for a cartilage and bone repair.

The current method provides a solution to the above-outlined problems by implanting, during the first arthroscopic surgery, a bone-inducing composition or a carrier comprising said composition comprising a bone-inducing agents into the bone lesion and an acellular matrix implant into the cartilage lesion thereby providing, in one surgery, treatments for both the bone and cartilage defects.

D. Bone and Bone Defects

The restorative method according to this invention is additionally also suitable for repair of the skeletal bone lesions.

The skeletal bone lesions are lesions which are either solely or at least partially located in the skeletal part of the bone, that is the bone placed immediately below the subchondral bone region, as seen in FIG. 1C.

FIG. 1C is a schematic representation of the deep osteochondro-skeletal bone injury extending into the skeletal bone. The figure shows the positioning of the host cartilage, subchondral bone and the skeletal bone as well as emplacement of the acellular matrix implant into the osteochondral defect and the bone-inducing composition into the subchondral and skeletal bone defect. The scheme shows the cartilage lesion implantation site with the acellular matrix implanted therein surrounded by host cartilage with underlaying bone lesion in the subchondral bone. The bone-inducing composition or a carrier comprising said composition is deposited into the bone lesion. The carrier for this purpose may be any matrix described above but is preferably collagenous, hydrogel or a polymer of an aromatic organic acid containing structure. Emplacement of the top and bottom sealant are also shown wherein the bottom sealant separates the bone portion of the defect from the cartilage lesion such that each is treated separately using different means.

In an alternative, the bone-inducing composition and/or the acellular implant carrier comprising such composition can be used for treatment of simple skeletal bone defects, lesions or fractures without a need for cartilage implant.

If and when the method of the invention is used for treatment of skeletal bone lesions, the bone-inducing composition alone or incorporated into a carrier, preferably dissolved in collagen or another binding agent, is deposited directly into the skeletal bone lesion. The bone-inducing agent is selected from the group consisting of calcium phosphate, hydroxyapatite, organoapatite, titanium oxide, demineralized bone powder, poly-L-lactic, polyglycolic acid or a copolymer thereof and a bone morphogenic protein.

A preferred bone-inducing agent is the demineralized bone powder (DMB). DMB is derived from bone by, for example, acid extraction of the calcium phosphate. Following such extraction, the DMB retains, in addition to the bone collagen other chemical elements found in the bone, including the naturally present members of TGF-β superfamily of bone development factors. These factors may also be extracted by further treatment of bone with such materials as quanidine hydrochloride. When these naturally occurring TGF-βs are present in the DMB, no further bone-inducing agents are needed to be present because DMB has a porous microstructure suitable for bone formation.

It is to be understood that the DMB itself is very light powder and therefore, it is preferably formulated in an agent having a binding capabilities. The most preferred binding agent is collagen or collagen-like agents, hydrogels, alginates, etc.

II. An Acellular Matrix Implant for Treatment of Cartilage Lesions

The current invention provides a method for treatment of injured, damaged, diseased or aged cartilage. To this end, the method involves implantation of the acellular matrix implant into the injured, damaged, diseased or aged cartilage at a site of injury or at a site of a defect caused by disease or age, in a single surgery. The acellular matrix implant is a collagenous construct or a polymer of an aromatic organic acid comprising various components as described below.

A. Preparation of an Acellular Matrix Implant

Preparation of the acellular matrix implant for implanting into the cartilage lesion involves preparation of acellular support matrix, typically a collagenous scaffold or sponge, thermo-reversible gelation hydrogel or a polymer of an aromatic organic acid and implanting said matrix into the cartilage defect in situ.

Figure 2A:
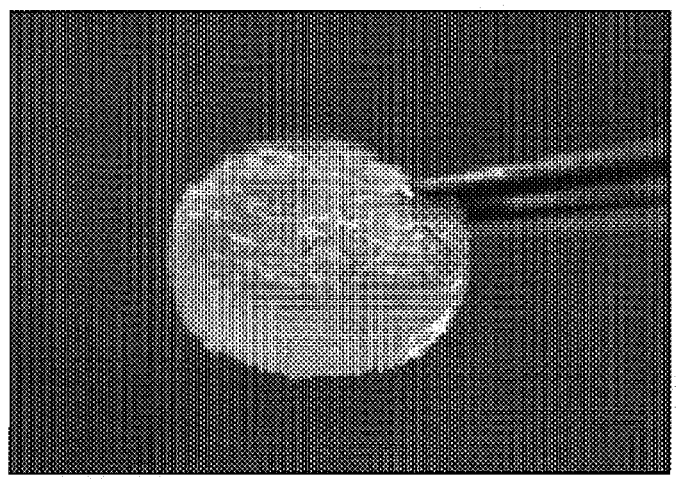
FIG. 2A is an image of an acellular matrix implant held in the forceps. The actual size of the sponge is 5 mm in diameter and 1.5 mm of thickness.
Figure 2B:
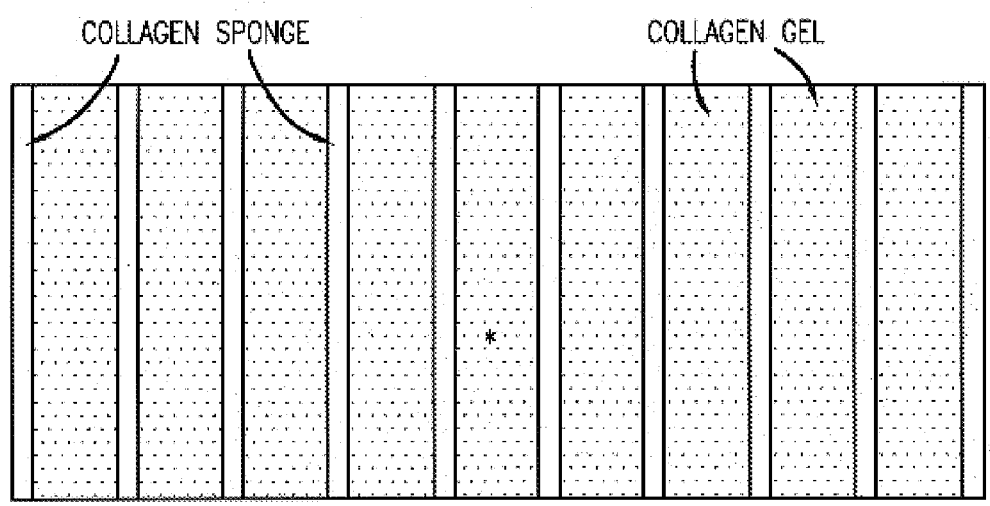
FIG. 2B is a longitudinal scheme of a honeycomb structure of an acellular matrix implant showing a relative localization of collagen sponge and porous collagen gel wherein the pore size is between 200 and 400 µm.

The acellular matrix implant, such as the one seen in FIG. 2A, is prepared according to the method of the invention and implanted into artificially generated lesions in a swine's knee weight bearing region. FIG. 2A is an image of an actual acellular matrix sponge implant used for implantation, here held in the forceps. The sponge has a size of 5 mm in diameter and 1.5 mm in thickness and comprises a composition of collagen sponge and collagen gel having pores of sizes from about 200–400 μm (FIG. 2B). When the sponge is implanted into the lesion, chondrocytes are activated and migrate into the porous structure of the sponge where they begin to secrete a new extracellular matrix ultimately replacing the collagen sponge and gel with the new hyaline cartilage. The sponge and gel naturally biodegrade and are metabolically removed from the lesion.

FIG. 2B is a cross-side view scheme of a honeycomb structure of the acellular matrix sponge seen in FIG. 2A illustrating a relative positioning of the collagen sponge, collagen gel and pores within the acellular matrix sponge.

The matrices of the acellular matrix implant deposited into the lesion are comprised of biodegradable materials which permit said implant to function for certain period of time needed for formation of the hyaline cartilage. Such biodegradable materials are subsequently biodegraded and metabolically removed from the site of implantation leaving, if any, only non-toxic residues. These materials were additionally found to promote formation of the superficial cartilage layer which covers the lesion containing the implant thereby protecting a newly formed hyaline cartilage. The biodegradable materials may additionally include enzymes, such as metalloproteinases, paracrine or autocrine growth hormones, GAG-lyases and such like enzymes, soluble protein mediators and other supplements. Presence or addition of these materials may enhance activation of mature, metabolically active but non-dividing chondrocytes present in the surrounding native host cartilage and migration of these chondrocytes from the native host cartilage surrounding the lesion cavity into said acellular matrix implant emplaced within said lesion.

The present invention thus concerns a discovery that when the acellular matrix implant according to the invention is implanted into a cartilage defect, under conditions described below, the older inactive chondrocytes residing within the surrounding native cartilage are induced to migrate into the defect where these chondrocytes are activated from static non-dividing stage to an active stage where they divide, multiply, promote growth of the extracellular matrix and generate a new hyaline cartilage in situ. Following the implantation of the acellular matrix implant, the cartilage defect is quickly repaired, particularly in the young individuals, by chondrocyte migration and by formation of the extracellular matrix supported by the metalloproteinases naturally present in sufficient amounts in tissues of the young individuals. For the repair of lesions in older subjects, the GAG-lyases and metalloproteinases, growth factors and other components are added or incorporated into said matrix before implantation or they may be conveniently used to coat said matrix to promote degradation of the injured cell.

A process for activation of chondrocytes was found to require certain period of time, typically from about 1 hour to about 3 weeks, typically only about 6 hours to about 3 days. The process for complete replacement of the implant matrix with the hyaline cartilage typically takes from one week to several months provided that the treated individual becomes normally physically active subjecting said new cartilage to the intermittent hydrostatic pressure by, for example, walking, running or biking.

B. Induction of Chondrocyte Migration

Induction of chondrocyte migration from the surrounding native cartilage involves biological actions of various agents either naturally present within the cartilage, cartilage surrounding tissue, blood or plasma or they are added either before, during or after the surgery to promote release, activation and migration of chondrocytes from the native surrounding host cartilage into the implant.

One of the steps in achieving the activation of the chondrocytes is the use of sealants at the top and bottom of the articular cartilage lesion. This step results in creation of a cavity into which the acellular matrix implant is deposited. A container-like porous property of the acellular collagenous matrix implant permits infusion and concentration of soluble protein mediators, enzymes, growth or other factors, etc., naturally present in the host's surrounding healthy cartilage.

Sealing of the top and bottom of the defect before and after insertion of the acellular matrix implant results in accumulation of autocrine and paracrine growth factors that are released by chondrocytes in the adjacent extracellular matrix, enabling these factors to induce cell migration into the implant. Suitable growth factors include, among others, certain transforming growth factors, platelet-derived growth factors, fibroblast growth factors and insulin-like growth factor-I. Additionally, these and other supplements, such as the GAG-lyases (matrix remodeling enzymes), may be used to coat the implant before its insertion into the lesion or the lesion itself may be coated.

The acellular matrix implant sequestered within the lesion cavity by the top and bottom sealant, however, remains in flowable communication with the adjacent cartilage. This arrangement creates conditions resulting in decrease of levels of inhibitors of the matrix remodeling enzymes, such as tissue inhibitors of metalloproteinase-1 (TIMP-1), metalloproteinase-2 (TIMP-2) and metalloproteinase-3 (TIMP-3), at the defect site. As a consequence, the matrix metalloproteinases (MMP-1, MMP-2, MMP-3) become accessible to enzymatic activation and degrade the adjacent extracellular matrix thereby releasing chondrocytes localized therein resulting in chondrocytes migration from the surrounding host cartilage into the acellular matrix implant or coat the walls of the lesion itself with the sugar lyases.

The acellular matrix implant sealed within the lesion also becomes a repository of exogenous growth factors that pass through the bottom sealant layer in response to joint loading and hydrostatic pressure to which the joint is subjected when undergoing a normal physical activity such as walking, running or biking. Consequently, in response to the hydrostatic pressure load, these factors become more concentrated within the defect site and chondrocytes released from adjacent areas of the surrounding extracellular matrix migrate into the lesion with ensuing chondrocyte proliferation and initiation of the de novo extracellular matrix synthesis within the lesion.

Moreover, the acellular matrix of the implant fills the defect with a material that has a reduced stiffness relative to normal articular cartilage and permits deformation of the adjacent native cartilage matrix edges thereby increasing level of shear stress further resulting in increased release of soluble mediators that indicate matrix remodeling and chondrocyte migration into the acellular matrix implant.

The presence of the acellular matrix implant sealed to the adjacent cartilage boundaries thus creates conditions by which matrix remodeling enzymes, namely matrix metalloproteinases, aggrecanases and cathepsins, become concentrated at the defect site and initiate enzymatic opening of the adjacent extracellular matrix so that chondrocytes may migrate into the acellular matrix implant, be deposited within its matrix, begin to divide and proliferate and secrete the new extracellular matrix, ultimately leading to formation of normal healthy hyaline cartilage.

C. Types of Acellular Matrix Implant

The acellular matrix implant provides a structural support for migration, growth and two or three-dimensional propagation of chondrocytes in situ. Generally, the acellular matrix is biologically biocompatible, biodegradable, hydrophilic and preferably has a neutral charge.

Typically, the implant is a two or three-dimensional structural composition, or a composition able to be converted into such structure, containing a plurality of pores dividing the space into a fluidically connected interstitial network. In some embodiments the implant is a sponge-like structure, honeycomb-like lattice, sol-gel, gel or thermo-reversible gelation hydrogel.

Typically, the implant is prepared from a collagenous gel or gel solution containing Type I collagen, Type II collagen, Type IV collagen, gelatin, agarose, hyaluronin, cell-contracted collagens containing proteoglycans, polymers of organic aromatic acids, glycosaminoglycans or glycoproteins, fibronectins, laminins, bioactive peptide growth factors, cytokines, elastins, fibrins, synthetic polymeric fibers made of poly-acids such as polylactic, polyglycotic or polyamino acids, polycaprolactones, polypeptide gels, copolymers thereof and combinations thereof. Preferably, the implant matrix is a gel, sol-gel, a polymer of an aromatic organic acid or a polymeric thermo-reversible gel. Most preferably the implant matrix contains aqueous Type I collagen.

The acellular matrix implant may be of a type of sponge, scaffold or honeycomb sponge, scaffold or honeycomb-like lattice or it may be a gel, sol-gel or thermo-reversible gel composition or it may be a polymer of an aromatic organic acid.

The acellular matrix implant may be produced as two or three-dimensional entities having an approximate size of the lesion into which they are deposited. Their size and shape is determined by the shape and size of the defect.

a. Acellular Sponges or Sponge-Like Implants

In general, any polymeric material can serve as the support matrix, provided it is biocompatible with tissue and possesses the required geometry. Polymers, natural or synthetic, which can be induced to undergo formation of fibers or coacervates, can be freeze-dried as aqueous dispersions to form sponges.

In addition to collagen, a wide range of polymers may be suitable for the fabrication of sponges, including agarose, hyaluronic acid, alginic acid, dextrans, polyHEMA, and poly-vinyl alcohol alone or in combination.

Typically, such sponges must be stabilized by cross-linking, such as, for example, ionizing radiation. Practical example includes preparation of freeze-dried sponges of poly-hydroxyethyl-methacrylate (pHEMA), optionally containing additional molecules, such as gelatin, advantageously entrapped within. Incorporation of agarose, hyaluronic acid, or other bio-active polymers can be used to modulate cellular responses. All these types of sponges can function advantageously as implant matrices for the purposes of the present invention.

The gel or gel solution used for preparation of the sponge or sponge-like implant is typically washed with water and subsequently freeze-dried or lyophilized to yield a sponge like matrix able to incorporate the migrating chondrocytes within the matrix. The acellular matrix implant of the current invention acts like a porous sponge when infiltrated with the migrating chondrocytes wherein the cells are distributed within the sponge pores, providing a mesh-like support permitting the chondrocytes to migrate and settle there, begin to divide and proliferate and secrete materials for generation of new extracellular matrix and eventually for generation of hyaline cartilage contiguous with the existing healthy surrounding cartilage.

One important aspect of the sponge implant is the pore size of the sponge matrix. Sponges having different pore sizes permit faster or slower infiltration of the chondrocytes into said sponge, faster or slower growth and propagation of the cells and, ultimately, the higher or lower density of the cells in the implant. Such pore size may be adjusted by varying the pH of the gel solution, collagen concentration, lyophilization conditions, etc., during implant fabrication. Typically, the pore size of the sponge is from about 50 to about 500 μm, preferably the pore size is between 100 and 300 μm and most preferably about 200 μm.

The pore size of the acellular matrix implant will be selected depending on the recipient. In the young recipient where the metalloproteinases are present naturally and active, the pore size will be smaller as the activated chondrocytes will rapidly proliferate through the pores and secrete extracellular matrix. In older recipients, the pores will be bigger as the migrating chondrocytes will be sluggish and will need more time to settle in the pores and proliferate.

An exemplary acellular matrix implant made of collagen is seen in FIG. 2. FIG. 2A is an example image of acellular collagenous matrix implant of size 4 mm in diameter and of 1.5 mm in thickness. The seeding density of this implant is between 300,000–375,000 chondrocytes per 25 μl volume corresponding to about 12–15 millions cells/ml. The cell density following the implantation of the acellular matrix implant is, of course, dependent on the rapidity of the migration of chondrocytes from the surrounding native cartilage and on their ability to divide and rapidity of their multiplication, however, the collagenous matrix of the implant has a capacity to accommodate this range of migrating cells.

The acellular sponge may be prepared according to procedures described in Example 1, or by any other procedure, such as, for example, procedures described in the U.S. Pat. Nos. 6,022,744; 5,206,028; 5,656,492; 4,522,753 and 6,080,194 or in co-pending application Ser. Nos. 10/625,822, 10/625,245 and 10/626,459, herein incorporated by reference.

b. Acellular Scaffold or Honeycomb Implants

One type of the implant of the invention is an acellular scaffold, honeycomb scaffold, honeycomb sponge or honeycomb-like lattice. All these implants contain a honeycomb-like lattice matrix providing a support structure for migrating and dividing chondrocytes. The honeycomb-like matrix is similar to that of the sponge described above but has that typical pattern of the honeycomb. Such honeycomb matrix provides a growth platform for the migrating chondrocytes and permits three-dimensional propagation of the migrated and divided chondrocytes thereby providing a structural support for formation of new hyaline cartilage.

FIG. 2B is a side view scheme of honeycomb structure of acellular matrix showing a collagen sponge and collagen gel with pore (*) size of each column of about 200–400 μm.

The honeycomb-like matrix is fabricated from a polymerous compound, such as collagen, gelatin, Type I collagen, Type II collagen or any other polymer, as described above for the sponge, having a desirable properties. In the preferred embodiment, the honeycomb-like acellular matrix implant is prepared from a solution comprising Type I collagen.

The pores of the honeycomb-like implant are evenly distributed within said honeycomb matrix to form a structure able of taking in and evenly distributing the migrated chondrocytes.

One preferred type of acellular matrix implant is Type-I collagen support matrix fabricated into a honeycomb-lattice, commercially available from Koken Company, Ltd., Tokyo, Japan, under the trade name Honeycomb Sponge.

Acellular matrix implant of the invention thus may be any suitable biodegradable structure, gel or solution, preferably containing collagen. For the purposes of convenience in implanting, such implant is typically a gel, preferably sol-gel transitional solution which changes the state of the solution from liquid sol to solid gel above room temperature. The most preferred such solution is the thermo-reversible gelation hydrogel or a thermo-reversible polymer gel as described below.

c. Sol-Gel Acellular Matrix Implant

Another type of acellular matrix implant is the implant matrix fabricated from sol-gel materials wherein said sol-gel materials can be converted from sol to gel and vice versa by changing temperature. For these materials the sol-gel transition occurs on the opposite temperature cycle of agar and gelatin gels. Thus, in these materials the sol is converted to a solid gel at a higher temperature.

Sol-gel material is a material which is a viscous sol at temperatures below 15° C. and a solid gel at temperatures around and above 37° C. Typically, these materials change their form from sol to gel by transition at temperatures between about 15° C. and 37° C. and are in a transitional state at temperatures between 15° C. and 37°. However, by changing the hydrogel composition, the transition temperature of the sol-gel may be predetermined to be higher or lower than those given above. The most preferred materials are Type I collagen containing gels and a thermo-reversible gelation hydrogel (TRGH) which has a rapid gelation point.

In one embodiment, the sol-gel material is substantially composed of Type I collagen and, in the form of 99.9% pure pepsin-solubilized bovine dermal collagen dissolved in 0.012 N HCl, commercially available under the trade name VITROGEN® from Cohesion Corporation, Palo Alto, Calif. One important characteristic of this sol-gel is its ability to be cured by transition into a solid gel form wherein said gel cannot be mixed or poured or otherwise disturbed thereby forming a solid structure optionally containing other components supporting the chondrocytes activation and migration. Sterile collagen for tissue culture may be additionally obtained from other sources, such as, for example, Collaborative Biomedical, Bedford, Mass., and Gattefosse, SA, St. Priest, France.

Type I collagen sol-gel is generally suitable and preferred material for fabrication of an acellular sol-gel implant.

d. Thermo-Reversible Gelation Hydrogel Implants

Additionally, the acellular matrix implant may be prepared from thermo-reversible materials similar to sol-gel which materials, however, have much faster point of transition, without hysteresis, from sol to gel and vice versa.

The thermo-reversible property is important for implantation of the acellular matrix implant into the lesion cavity as it may be implanted into the lesion cavity in its sol state whereby filling said cavity with the sol wherein the sol forms itself according to the exact shape of the cavity leaving no empty space or being too large or too small, as the case may be, for a prefabricated sponge or a honeycomb lattice. Following the warming of the sol emplaced within the articular lesion cavity to the natural body temperature, the sol instantly transitions and becomes solid gel providing a structural support for the migrating chondrocytes from the surrounding native cartilage.

One characteristic of the sol-gel is its ability to be cured or transitioned from a liquid into a solid form and vice versa. This property may be advantageously used for solidifying the liquid or liquefying the solid gel acellular matrix implant within the cartilage lesion as well as for delivery, storing or preservation purposes of said acellular matrix implant. Additionally, these properties of sol-gel also permit its use as a support matrix by changing its sol-gel transition by increasing or decreasing temperature in the lesion, or exposing the sol-gel to various chemical or physical conditions or ultraviolet radiation.

In one embodiment, the acellular matrix implant is a thermo-reversible gelation hydrogel or gel polymer kept stored and implanted at temperatures between 5° C. and 15° C. At that temperature, the hydrogel is at a liquid sol stage and permits easy emplacement into the lesion as the sol. Once the sol is emplaced within the lesion, the sol is naturally or artificially subjected to higher temperature of about 30° C. and 37° C. at which temperature the liquid sol solidifies into solid gel. The gelling time is from about several minutes to several hours, typically about 1 hour. In such an instance, the solidified gel may itself become and be used as an implant or this sol may be loaded into a separate support matrix, such as a sponge or scaffold honeycomb implant.

The primary characteristic of the thermo-reversible gelation hydrogel (TRGH) is that upon its degradation within the body it does not leave biologically deleterious material and that it does not absorb water at gel temperatures. TRGH has a very quick sol-gel transformation which requires no cure time and occurs simply as a function of temperature without hysteresis. The sol-gel transition temperature can be set at any temperature in the range from 5° C. to 70° C. by the molecular design of the thermo-reversible gelation polymer (TGP), a high molecular weight polymer, of which less than 5 wt % is enough for hydrogel formation.

The thermo-reversible gelation hydrogel (TRGH), should be compressively strong and stable at 37° C. and below till about 32° C., that is to about temperature of the synovial capsule of the joint which is typically below 37° C., but should easily solubilize below 30–31° C. to be able to be conveniently changed to the sol within the lesion cavity. The compressive strength of the TRGH must be able to resist compression by the normal activity of the joint.

The typical TRGH is generally made of blocks of high molecular weight polymer comprising numerous hydrophobic domains cross-linked with hydrophilic polymer blocks. TRGH has a low osmotic pressure and is very stable as it is not dissolved in water when the temperature is maintained above the sol-gel transition temperature. Hydrophilic polymer blocks in the hydrogel prevent macroscopic phase separation and separation of water from hydrogel during gelation. These properties make it especially suitable for safe storing and extended shelf-life.

In this regard, the thermo-reversible hydrogel is an aqueous solution of thermo-reversible gelation polymer (TGP) which turns into hydrogel upon heating and liquefies upon cooling. TGP is a block copolymer composed of temperature responsive polymer (TRP) block, such as poly(N-isopropylacrylamide) or polypropylene oxide and of hydrophilic polymer blocks such as polyethylene oxide.

Thermally reversible hydrogels consisting of co-polymers of polyethylene oxide and polypropylene oxide are available, for example, from BASF Wyandotte Chemical Corporation under the trade name of Pluronics.

In general, thermo-reversibility is due to the presence of hydrophobic and hydrophilic groups on the same polymer chain, such as in the case of collagen and copolymers of polyethylene oxide and polypropylene oxide. When the polymer solution is warmed, hydrophobic interactions cause chain association and gelation; when the polymer solution is cooled, the hydrophobic interaction disappears and the polymer chains are dis-associated, leading to dissolution of the gel. Any suitably biocompatible polymer, natural or synthetic, with such characteristics will exhibit the same reversible gelling behavior.

e) Acellular Gel Implants

The acellular matrix implants of the invention may alternatively be prepared from various gel materials, such as suspending gels, not necessarily thermo-reversible, which are commercially available and may be suitable for use as acellular matrix implants as long as they are biodegradable.

One example of such gel is polyethylene glycol (PEG) and its derivatives, in which one PEG chain contains vinyl sulfone or acrylate end groups and the other PEG chain contains free thiol groups which covalently bond to form thio-ether linkages. If one or both partner PEG molecules are branched (three- or four-armed), the coupling results in a gel network. If the molecular weight of the PEG chains used for the implant preparation is between 500 and 10,000 Daltons along any linear chain segment, the network will be open and suitable for receiving migrating chondrocytes, swellable by interstitial water, and compatible with living chondrocytes.

The coupling reaction of PEG can be accomplished, for example, by preparing 5 to 20% (w/v) solutions of each PEG separately in aqueous buffers or cell culture media. Just prior to implantation, thiol, PEG and the acrylate or vinyl sulfone PEG are mixed and infused into the lesion. Gelation will begin spontaneously in 1 to 5 minutes. The rate of gelation can be modulated somewhat by the concentration of PEG reagent and by pH. The rate of coupling is faster at pH 7.8 than at pH 6.9. Thus, by modifying the pH of the PEG containing mixture, the gelation process may be controlled to be faster or slower, as desired by the surgeon. Such gels are, however, typically not degradable within the body unless the additional ester or labile linkages are incorporated into the chain. PEG reagents may be purchased from Shearwater Polymers, Huntsville, Ala., USA; or from SunBio, Korea.

In a second alternative, the gelling material may be alginate. Alginate solutions are gellable in the presence of calcium ions. This reaction has been employed for many years to suspend cells in gels or micro-capsules. A solution of alginate (1–2%; w/v) in culture media devoid of calcium or other divalent ions is mixed in a solution containing calcium chloride which will gel the alginate. Analogous reactions can be accomplished with other polymers which bear negatively charged carboxyl groups, such as hyaluronic acid. Viscous solutions of hyaluronic acid can be gelled by diffusion of ferric ions.

f. A Polymer of an Aromatic Organic Acid Matrix

The acellular implant may also conveniently be made of a polymer of an aromatic organic acid. Polymers of this type have typically a negative charge and are thus preferred for use as a bone-inducing composition carriers. However, these type of compounds may also be used and are suitable for use as cartilage acellular implants.

G. Biodegradable Implant

The acellular matrix implant of the invention is a temporary structure intended to provide a temporary supporting for the migrating, dividing, proliferating and extracellular matrix secreting chondrocytes released from the surrounding cartilage.

Consequently, the implant of the invention must be fully biodegradable. Whether it is a sponge, honeycomb lattice, sol-gel or TRGH, in time, the delivered implant is disintegrated or incorporated into the existing cartilage and the TRGH is subsequently degraded leaving no undesirable debris behind.

Overall, any of the acellular matrix implants for cartilage defects described above is suitable for implantation into a cartilage lesion of any size and shape and provides a support for a structural rebuilding of the cartilage by migrating chondrocytes therein from the surrounding healthy host cartilage. The implantation of the implant of the invention results in the generation of normal healthy hyaline cartilage and in complete healing of the cartilage defect.

III. Osteochondral Defects and Treatment Thereof

Lesions of the articular cartilage are often accompanied by lesions of the underlying bone. Such defects are thus a composite of cartilage and underlying bone. These defects are herein cumulatively called osteochondral defects.

A. Method for Treatment of Osteochondral Defects

The osteochondral defects are caused by injury of the cartilage and bone. The cartilage and bone are histologically two different connective tissues, as described above. Consequently, it is not possible to effectively treat both using the same methods and means and such treatment is thus complex and more difficult than a treatment of the cartilage lesion or chipped bone alone. Furthermore, bone development can influence cartilage development such that it acts as a barrier to further cartilage development during its critical developmental stages.

In one attempt to treat these complex injuries, a mosaicplasty technique was developed. The mosaicplasty, as already mentioned above, involves a removal of grafts from the healthy tissue and plugging such grafts into the both bone and cartilage lesions. An obvious defect of this technique is that in order to treat the injured site, surgeon has to remove, during the open surgical procedure, a healthy tissue from another site thereby disrupting the healthy tissue in the process.

When, however, the method of the current invention is used to treat these complex osteochondral injuries, it is possible to treat both the bone and cartilage lesions during the same surgery without need to remove and disturb the healthy tissue and/or undergo multiple surgeries required, for example, for allograft transplantation and other techniques.

The current method permits such dual treatment simultaneously by implantation of, in combination, an acellular matrix implant and a bone-inducing composition or a carrier comprising said composition comprising a bone-inducing agents further, preferably, in combination with biologically acceptable sealants.

In practice, during the same surgery, the surgeon first debrides both lesions and deposits the bone-inducing composition or a carrier comprising said composition into the bone lesion and covers said bone lesions with one or several layers of a biologically acceptable sealant, preferably a modified highly polymerizable sealant selected from those described below in section IV. After the sealant polymerizes, typically within several minutes, preferably between 0.5 and 5 minutes, the acellular matrix implant is deposited into the cartilage lesion and covered with yet another layer of the sealant, herein called the top sealant. In this way, the bone-inducing composition or a carrier comprising said composition is sequestered within the bone lesion and the bone forming agents, such as, for example, demineralized bone powder, calcium phosphates, calcium citrate, hydroxyapatite, organoapatite, titanium oxide, polyacrylate, alone or in combination, and a bone morphogenic protein and/or other known bone-inducing agents act as inducement for osteoblast migration from the surrounding bone without interference from the acellular matrix implant. As a consequence of this separation of the bone and cartilage lesion, there is no invasion of the hyaline cartilage or formation of fibrocartilage in the bone lesion.

Conversely, when the acellular implant is separated from the bone-inducing composition or a carrier comprising said composition, there is no interference from any of the bone-inducing agents with the chondrocyte migration, extracellular matrix formation and generation of the hyaline cartilage. Each the bone and the cartilage are treated separately and yet simultaneously during one arthroscopic surgery.

The sealant may be deposited, preferably, as is, that is without any additional agents being added, or it may be added to the bone-inducing composition or a carrier comprising said composition, if desirable.

The bone-inducing composition or a carrier comprising said composition deposited within the bone defect covered with the sealant is left in the lesion in order to achieve the bone reconstruction and growth. Both the composition and the sealant are aiding in a bone natural healing.

The acellular matrix implant implanted within the cartilage defect separated from the bone lesion by a layer of the sealant and covered with the top sealant is left in the cartilage lesion until it biodegrades when the hyaline cartilage replacement is formed in order to achieve the chondrocyte migration and formation of extracellular matrix.

A typical process for repair of osteochondral defects is the cleaning and debridement the osteochondral defect, depositing the bone-inducing composition or a carrier comprising said composition containing the bone-inducing agents, up to the upper limit of the lesion in subchondral bone, applying a layer of the sealant over the composition and letting the sealant to polymerize. After the sealant polymerizes, typically in from about 0.2 to about 10 minutes, preferably about 0.5–5 minutes, the surgery proceeds with implanting the acellular matrix implant into the cartilage lesion, as described above. The cartilage lesion containing the implant is then covered with yet another layer of the sealant (top sealant) to seal and protect the wound from the exterior.

The above described procedure is particularly suitable for treatment of osteochondral injuries as it permits dual treatment under different conditions being implemented during the same surgery.

One specific case of osteochondral defects is osteochondritis dissecans, where a focal lesion of the bone and cartilage results in a loose or totally dislocated osteochondral fragment. Currently the only available treatment requires three independent surgeries including biopsy harvesting of periosteum (first surgery), culturing cells, removal of the loose fragment (second surgery), introduction of the cultured cells into the lesion and bone-grafting (third surgery).

The current method, as described above, or modified to include a step of the fragment removal, during a single surgery, eliminates a need for two or three surgeries, as all steps necessary for repair of the osteochondritis dissecans are performed at the same time during one surgery.

B. Bone-Inducing Agents

Bone-inducing agents are compounds or proteins having a definite ability to promote formation of the bone.

The most suitable bone forming agents are demineralized bone powder (DMP), calcium phosphate, calcium citrate, hydroxyapatite, organoapatite, titanium oxide and growth factors, namely a group of growth factors known as bone morphogenic proteins, fibroblast growth factor (FGF), platelet derived growth factor (PDFG), epithelial growth factor (EGF), glioma derived factor (GDF) and transforming growth factor beta-1 (TGF-β1). These growth factors may be used individually and/or in combination with each other or with other bone-inducing factors.

The demineralized bone powder is particularly suitable to be used as a bone-inducing composition or as a bone-inducing carrier and no other compounds are needed to serve as bone inducer or supporting structure and necessary because the demineralized bone powder mimics microporous structure of the bone. Before depositing the DMB into the bone or subchondral bone lesion, the DMB may be conveniently dissolved in collagen or some other adhesive fluid or hydrogel which will permit its deposition into the lesion but itself will have no bone-inducing function. The used amount of DMB is such that is makes a concentrated highly viscous paste. The used amount depends on the structure and grind of the DMB.

Bone morphogenic proteins are typically identified by the abbreviation BMP and are further distinguished from each other by numbering, such as BMP-2, BMP-3, BMP-4, BMP-5, BMP-6, BMP-7, BMP-8 and BMP-14. Some of them are further identified by a generic name, such as, for example BMP-3 is called osteogenin, BMP-3B is GDF-10, etc. The bone morphogenic proteins are administered generally in concentration (per carrier volume or weight) of from about 0.01 to about 5 mg/cm$^3$, preferably from about 0.1 to about 1.5 mg/cm$^3$ or from about 0.01 mg/g to about 5 mg/g, preferably from about 0.1 mg to about 2.5 mg/g.

C. Bone-Inducing Composition

The bone-inducing composition or a carrier comprising said composition of the invention comprises one or several bone-inducing agents as listed above, in concentrations as disclosed. The bone-inducing composition may be administered as a powder, solution, gel, sol-gel, TRGH mixed in concentration given above or incorporated into a structure similar to that of the acellular implant, pre-prepared and implanted into the bone lesion or fracture. The composition prepared as TRGH, for example, is prepared as a sol solution and administered as such. The sol subsequently changes its state into the gel filling out the whole bone lesion. The bone-inducing agents may also be dissolved in PEG, collagen, alginate, etc., and deposited as such. It could also be soaked up in a second sponge system like the acellular matrix sponge described above.

The preferred mode for the deposition of the bone-inducing agents into the osteochondral or bone lesion is to dissolve the agent in a gel, such as diluted collagen, alginate and such like gels.

D. Bone-Inducing Carrier

A bone-inducing carrier or a carrier comprising bone-inducing composition is a carrier compound which is suitable for depositing said bone-inducing composition comprising at least one bone-inducing agent or, preferably, a combination of several agents into a bone lesion. Typically, the carrier will be a biodegradable porous matrix, hydrogel, sponge, honeycomb, or scaffold having large pores from about 50 to about 150 μm, which pores encourage migration of osteoblast. The carrier will also have an interconnecting small pores of about 0.1 to about 10 μm which connect the large pores, permit the osteoblast to settle within the carrier and provide a supporting matrix and connecting microstructure for supply of nutrient and other factors thereby permitting the bone formation. The surface of such carrier might be negatively charged encouraging pseudopod attachment of osteoblasts and their migration into the carrier resulting in the bone formation.

IV. Biologically Acceptable Sealants

Generally, the implant is implanted into the cartilage or bone lesion and between at least two layers, of top and bottom of biologically acceptable adhesive sealants.

In practice, the first (bottom) layer of the sealant is introduced into the lesion and deposited at the bottom of the lesion. The first sealant's function is to prevent entry and to block the migration of subchondral and synovial cells of the extraneous components, such as blood-borne agents, cell and cell debris, etc. Before the implant is deposited, such debris could interfere with the integration of the acellular matrix implant. The second function of the first sealant is to contain enzymes, hormones and other components which are naturally present in the lesion and which are needed for chondrocyte activation, migration, secretion of other agents and proliferation of newly formed extracellular matrix and hyaline cartilage. Then the acellular matrix implant is implanted over the first sealant. The second (top) sealant layer is placed over the acellular matrix implant. The presence of both these sealants in combination with the acellular matrix implant results in successful activation of chondrocytes, their migration and integration into the implant matrix and ultimately in new formation of joint hyaline cartilage.

A. A First—Bottom Sealant

In a method for treatment of cartilage lesions, the first (bottom) sealant forms an interface between the introduced implant and the native tissue, such as subchondral bone or cartilage. The first sealant, deposited at the bottom of the lesion, must be able to contain migrating chondrocytes within the lesion, to protect the implant from influx of undesirable agents and to prevent chondrocyte migration into the sub-chondral space. Additionally, the first sealant prevents the infiltration of blood vessels and undesirable cells and cell debris into the implant and it also prevents formation of the fibrocartilage.

In a method for treatment of osteochondral defects, the first (bottom) sealant forms a barrier between the cartilage lesion and the bone lesion. Because these two defects are in two qualitatively different tissues they require different treatments. As described above, the bone lesion is treated with the bone-inducing composition or a carrier comprising said composition while the cartilage lesion is treated with the acellular matrix implant. Moreover, it is not desirable that the enzymes present in the cartilage lesion activating chondrocyte migration mix with the bone-inducing agents and growth factors needed for bone lesion repair. When there is no separation of one tissue from another, it can easily end up with, for example, the fibrocartilage ingrowing into the bone area and, in such an instance, instead of bone being replaced with the bone, it is replaced with the inferior fibrocartilage. Consequently, for treatment of osteochondral defects, the bottom sealant is deposited over the bone lesion filled with the bone-inducing composition or a carrier comprising said composition separating the bone lesion from the cartilage lesion implanted with the acellular implant. In this way, each the acellular implant and the bone-inducing composition can work independently and without interference from the other.

B. A Second—Top Sealant

The second (top) sealant acts as a protector of the acellular matrix implant or the lesion cavity on the surface and is typically deposited over the lesion after the implant is deposited therein and in this way protects the integrity of the lesion cavity from any undesirable effects of the outside environment, such as invading cells or degradative agents and seals the acellular matrix implant gel in place after its deposition therein.

The second sealant also acts as a protector of the acellular implant implanted within a cavity formed between the two sealants. In this way, the second sealant is deposited after the implant is deposited over the first sealant and seals the implant within the cavity or it may be deposited over the space holding gel before the implant deposition.

The third function of the second sealant is as an initiator or substrate for the formation of a superficial cartilage layer.

Performed studies described below confirmed that when the second sealant was deposited over the cartilage lesion, a growth of the superficial cartilage layer occurred as an extension of the native superficial cartilage layer. This superficial cartilage layer was particularly well-developed when the lesion cavity was filled with the thermo-reversible gel or sol gel thereby leading to the conclusion that such gel might provide a substrate for the formation of such superficial cartilage layer.

C. Top and Bottom Sealant Properties

The first bottom or second top sealant used according to an embodiment of the invention must possess the following characteristics:

Sealant must be biologically acceptable, easy to use and possess required adhesive and cohesive properties.

The sealant must be biologically compatible with tissue, be non-toxic, not swell excessively, not be extremely rigid or hard, as this could cause abrasion of or extrusion of the sealant from the tissue site, must not interfere with the formation of new cartilage, or promote the formation of other interfering or undesired tissue, such as bone or blood vessels and must be bioresorbable and biodegradable by any acceptable metabolic pathway, or be incorporated into the newly formed hyaline cartilage tissue.

The sealant must rapidly gel from a flowable liquid or paste to a load-bearing gel within 3 to 15 minutes, preferably within 3–5 minutes. However, the sealant must not gel or polymerize too rapidly as it would cause problems with its even distribution over the lesion. Gelling faster than 30 seconds is undesirable. Longer gelation times are not compatible with surgical time constraints. Additionally, the overall mode of use should be relatively simple because complex and lengthy procedures will not be accepted by surgeons.

Adhesive bonding is required to attach the sealant formulation to tissue and to seal and support such tissue. Minimal possessing peel strengths of the sealant should be at least 3 N/m and preferably 10 to 30 N/m. Additionally, the sealant must itself be sufficiently strong so that it does not break or tear internally, i.e., it must possess sufficient cohesive strength, measured as tensile strength in the range of 0.2 MPa, but preferably 0.8 to 1.0 MPa. Alternatively, a lap shear measurement which define the bond strength of the formulation should have values of at least 0.5 N/cm$^2$ and preferably 1 to 6 N/cm$^2$.

Sealants possessing the required characteristics are typically polymeric. In the un-cured, or liquid state, such sealant materials consist of freely flowable polymer chains which are not cross-linked together, but are neat liquids or are dissolved in physiologically compatible aqueous buffers. The polymeric chains also possess side chains or available groups which can, upon the appropriate triggering step, react with each other to couple or cross-link the polymer chains together. If the polymer chains are branched, i.e., comprising three or more arms on at least one partner, the coupling reaction leads to the formation of a network which is infinite in molecular weight, such as for example, a gel.

The formed gel has cohesive strength dependent on the number of inter-chain linkages, the length expressed as molecular weight of the chains between links, the degree of inclusion of solvent in the gel, the presence of reinforcing agents, and other factors. Typically, networks in which the molecular weight of chain segments between junction points (cross-link bonds) is between 100–500 Daltons are tough, strong, and do not swell appreciably. Networks in which the chain segments are between 500–2500 Daltons swell dramatically in aqueous solvents and become mechanically weak. In some cases the latter gels can be strengthened by specific reinforcer molecules; for example, the methylated collagen reinforces the gels formed from 4-armed PEGs of 10,000 Daltons (2500 Daltons per chain segment).

The gel's adhesive strength permits bonding to adjacent biological tissue by one or more mechanisms, including electrostatic, hydrophobic, or covalent bonding. Adhesion can also occur through mechanical inter-lock, in which the uncured liquid flows into tissue irregularities and fissures, then, upon solidification, the gel is mechanically attached to the tissue surface.

At the time of use, some type of triggering action is required. For example, it can be the mixing of two reactive partners, it can be the addition of a reagent to raise the pH, or it can be the application of heat or light energy.

Once the sealant is in place, it must be non-toxic to adjacent tissue, and it must be incorporated into the tissue and retained permanently, degraded in situ, or be naturally removed, usually by hydrolytic or enzymatic degradation. Degradation can occur internally in the polymer chains, or by degradation of chain linkages, followed by diffusion and removal of polymer fragments dissolved in physiological fluids.

Another characteristic of the sealant is the degree of swelling it undergoes in the tissue environment. Excessive swelling is undesirable, both because it creates pressure and stress locally, and because a swollen sealant gel losses tensile strength, due to the plasticizing effect of the imbibed solvent which, in this case, is physiological fluid. Gel swelling is modulated by the hydrophobicity of the polymer chains. In some cases it may be desirable to derivatize the base polymer of the sealant so that it is less hydrophilic. For example, one function of methylated collagen containing sealant is presumably to control swelling of the gel. In another example, the sealant made from penta-erythritol tetra-thiol and polyethylene glycol diacrylate can be modified to include polypropylene glycol diacrylate, which is less hydrophilic than polyethylene glycol. In a third example, sealants containing gelatin and starch can also be methylated both on the gelatin and on the starch, again to decrease hydrophilicity.

D. Suitable Sealants

Sealants suitable for purposes of this invention include the sealants prepared from gelatin and dialdehyde starch triggered by mixing aqueous solutions of gelatin and dialdehyde starch which spontaneously react and gel.

In general, a sealant useful for the purposes of this application has adhesive, or peel strengths at least 10 N/m and preferably 100 N/cm; it needs to have tensile strength in the range of 0.2 MPa to 3 MPa, but preferably 0.8 to 1.0 MPa. In so-called "lap shear" bonding tests, values of 0.5 up to 4–6 N/cm$^2$ are characteristic of strong biological adhesives.

Such properties can be achieved by a variety of materials, both natural and synthetic. Examples of suitable sealant include gelatin and di-aldehyde starch described in PCT WO 97/29715, 4-armed pentaerythritol tetra-thiol and polyethylene glycol diacrylate described in PCT WO 00/44808, photo-polymerizable polyethylene glycol-co-poly(a-hydroxy acid) diacrylate macromers described in U.S. Pat. No. 5,410,016, periodate-oxidized gelatin described in U.S. Pat. No. 5,618,551, serum albumin and di-functional polyethylene glycol derivatized with maleimidyl, succinimidyl, phthalimidyl and related active groups described in PCT WO 96/03159.

Another acceptable sealant is made from a copolymer of polyethylene glycol and polylactide, polyglycolide, polyhydroxybutyrates or polymers of aromatic organic amino acids and sometimes further containing acrylate side chains, gelled by light, in the presence of some activating molecules.

The acceptable sealant made from periodate-oxidized gelatin remains liquid at acid pH, because free aldehyde and amino groups on the gelatin cannot react. To trigger gelation, the oxidized gelatin is mixed with a buffer that raises the pH to pH at which the solution gels.

Still another sealant made from a 4-armed pentaerythritol thiol and a polyethylene glycol diacrylate is formed when these two neat liquids (not dissolvable in aqueous buffers) are mixed.

Another type of the suitable sealant is 4-armed polyethylene glycol derivatized with succinimidyl ester and thiol plus methylated collagen in two-part polymer compositions that rapidly form a matrix where at least one of the compounds is polymeric, such as polyamino acid, polysaccharide, polyalkylene oxide or polyethylene glycol and two parts are linked through a covalent bond, for example a cross-linked PEG with methyl collagen, such as a cross-linked polyethylene glycol hydrogel with methyl-collagen, as described in U.S. Pat. Nos. 6,312,725B1 and 6,624, 245B2, hereby incorporated by reference. One drawback of the type of the bioadhesive described therein is that it gels and/or bonds extremely fast upon contact with tissue, particularly with tissue containing collagen. Consequently, this type of bioadhesive, which is designed for rapid gelling or bonding during vessel or tissue injury typically needs to be modified in order to prolong the gelling and/or bonding time to be suitable for use as a sealant of the invention.

One group of suitable sealants comprises albumin. Albumin containing sealants typically comprise at least human or bovine serum albumin conjugated with a cross-linking agent. The cross-linking agent may be selected from the group consisting of glutaraldehyde, amino acids, polypeptides and proteins. Further modification may include conjugation with a fibrous protein, such as collagen or with a gel compound although this portion of the sealant is, in the current invention, generally provided by the support matrix of the invention. Sealants and bioadhesives or portions thereof which fall within a category of this type of suitable sealants are disclosed in U.S. Pat. Nos. 6,310,036; 6,217,894 and 6,685,726, hereby incorporated by reference.

It is worth noting that it is not the presence or absence of particular protein or polymer chains, such as gelatin or polyethylene glycol, which necessarily governs the mechanical strength and degradation pattern of the sealant. The mechanical strength and degradation pattern are controlled by the cross-link density of the final cured gel, by the types of degradable linkages which are present, and by the types of modifications and the presence of reinforcing molecules, which may affect swelling or internal gel bonding.

The first and second sealant, or the sealant used for separation of the bone and cartilage lesions, must be a biologically acceptable, typically rapidly gelling and polymerizable synthetic compound having adhesive, bonding and/or gluing properties, and is typically a hydrogel, such as derivatized polyethylene glycol (PEG) which is preferably cross-linked with a collagen compound, typically alkylated collagen. The sealant used for separation of the bone and cartilage lesions should polymerize rapidly in order to permit surgeon to continue with the surgery without any delay. For the purposes of this invention, the sealant should have a tensile strength of at least 0.3 MPa.

Additionally, the sealant may be two or more polymer compositions that rapidly form a matrix where at least one of the compounds is polymer, such as, polyamino acid, polysaccharide, polyalkylene oxide or polyethylene glycol and two parts are linked through a covalent bond and cross-linked PEG with collagen. The sealant of the invention typically gels and polymerizes within about 0.5 to about 5 minutes upon contact with tissue, particularly with tissue containing collagen.

The second sealant or the sealant used for separation of the bone and cartilage lesions may or may not be the same as the first sealant and the first and second sealants may be utilized as a barrier between the bone and cartilage lesions but the different sealant may also be used for this purpose.

For the use in the current invention, the sealant is slowly polymerized in situ after its deposition at the bottom of the lesion or between the bone-inducing composition and acellular implant. Such slow polymerization is necessary to avoid uneven distribution of the sealant over the bottom of the lesion and also to avoid the random and uneven accumulation of the sealant on some parts of the surface while leaving other parts of the bottom surface uncovered. The primary function of the sealant is to protect the acellular implant from undesirable effects of migrating cells, tissue debris and various factors present in the blood or serum, as already discussed previously. Consequently, its even distribution over the bottom of the lesion or over the bone-inducing composition is of great importance and to achieve such even distribution, the polymerization of the sealant must not be too slow or too rapid in order to reach the bottom of the lesion, cover it and then polymerize in situ and still meet surgeon's time constraints. For arthroscopic surgery and implantation of the acellular implant, the sealant polymerization at the bottom of the implant site needs to occur between 30 seconds and about 5 minutes, preferably between 30 seconds and about 3 minutes.

V. Method for Formation of Superficial Cartilage Layer Over the Acellular Matrix Implant An accompanying aspect of this invention is a finding that when the acellular matrix implant produced according to procedures described above is implanted into a cartilage lesion cavity and covered with a biocompatible adhesive top sealant, the resulting combination leads to a formation of a superficial cartilage layer completely overgrowing said lesion.

In practice, the method for formation of the superficial cartilage layer comprises several steps. First, the bottom of the lesion is covered with a first, bottom sealant deposited as polymerizable solution. Following the sealant polymerization, the acellular matrix implant is implanted into said lesion and a second, top sealant is deposited over the implant. In one embodiment, the implant may be a thermo-reversible gel which easily changes from sol to gel at the body temperature thereby permitting an external preparation and delivery of the implant into the lesion. The gel is then covered with the top sealant which promotes formation of the superficial cartilage layer overgrowing the cartilage lesion thereby sequestering the implant within the lesion and protecting it from outside environment.

The superficial cartilage layer begins to form very quickly after the implant is implanted into the cartilage lesion and covered with the top sealant layer. As shown in FIG. 6, two weeks after acellular matrix implantation superficial cartilage layer was observed on the surface of acellular matrix implanted site. FIG. 6 shows arthroscopic evaluation two weeks after the defect was made in the femoral condyle where the superficial cartilage layer is clearly visible compared to untreated empty defect made at the same time, seen in FIG. 5.

The top sealant gives support and promotes formation of the superficial cartilage layer in some instances further assisted by the gel components of the matrix. At the time when the implant matrix is completely degraded and the new hyaline cartilage is formed in the defect, the superficial cartilage layer completely covers and insulates the newly formed cartilage similarly to a synovial membrane naturally present and covering the joints. The second top sealant is eventually also biodegraded and removed from the site, not however, until the superficial cartilage layer, a synovial-like membrane, has formed over.

VI. Method for Use of Acellular Matrix Implant

The method for repair and restoration of damaged, injured, diseased or aged cartilage to a functional cartilage is based on implantation of an acellular matrix implant into a cartilage lesion.

The method for use of the acellular matrix implant in these treatments comprises following steps:

a) Preparing an Acellular Matrix Implant

The first step involves preparation of the acellular matrix implant for implanting into the cartilage lesion. Preparation of acellular matrix implants is described in greater detail in sections II.A.

b) Selecting and Depositing the First and Second Sealant into the Cartilage Lesion The second step is optional and involves selection and depositing bottom and/or top sealant layers into a cartilage lesion.

Specifically, this step involves deposition of the first sealant at the bottom of the cartilage lesion and the second sealant over the acellular matrix implant. The first and the second sealants can be the same or different, however, both the first and the second sealants must have certain definite properties to fulfill their functions.

The bottom sealant, deposited into the lesion before the acellular matrix implant is introduced, acts as a protector of the lesion cavity integrity. It protects the lesion cavity from contamination by extraneous substances such as blood and tissue debris. It protects integrity of the naturally present enzymes and other mediators needed for and involved in formation of extracellular matrix and activation of chondrocytes and their migration from a surrounding host cartilage into the acellular implant implanted in the lesion. It also protects the lesion cavity from formation of the fibrocartilage.

The top sealant deposited over the implant and effectively sealing the lesion from external environment acts as a protector of the lesion cavity as well as a protector of the implant deposited within a lesion cavity formed between the two sealants as well as an initiator of the formation of the superficial cartilage layer.

c) Implanting the Acellular Matrix Implant

Next step in the method of the invention comprises implanting said acellular matrix implant into a lesion cavity formed between two layers of sealants.

The implant is preferably deposited into said lesion cavity after the bottom sealant is deposited but before the top sealant is deposited over it or the implant may be deposited into the lesion cavity without the bottom sealant being deposited there and then covered with the top sealant.

d) Generation of the Superficial Cartilage Layer

A deposition of the top sealant over the acellular matrix implant leads to sealing of the lesion cavity and overgrowth of said cavity with a superficial cartilage layer.

Typically, a biologically acceptable top sealant is deposited over the acellular matrix implant implanted into the lesion cavity. The second sealant acts as an initiator for formation of the superficial cartilage layer which in time completely overgrows the lesion and strongly resembles a healthy synovial membrane. In several weeks or months, usually in about two weeks, the superficial cartilage layer completely covers the lesion, protects the implant, migrating, dividing and proliferating chondrocytes and newly secreted extracellular matrix. Protecting the implant from extraneous environment permits integration of the newly formed cartilage tissue into the native surrounding cartilage substantially without formation of fibrocartilage.

Formation of the superficial cartilage layer is thus a very important aspect of the healing of the cartilage and its repair and regeneration.

VII. Method for Treatment of Cartilage Lesions

The method for treatment of damaged, injured, diseased or aged cartilage according to the invention is suitable for healing of cartilage lesions due to acute injury by providing conditions for regeneration of the healthy hyaline cartilage and for its integration into the surrounding native cartilage.

The method generally encompasses several novel features, namely, fabrication of a biologically acceptable biodegradable acellular matrix implant, selecting and depositing a top and bottom adhesive sealants to the lesion and the implantation of the acellular matrix implant within a cavity generated by two sealants, a formation of the superficial cartilage layer covering the lesion and protecting the integrity of the acellular matrix implant deposited therein, and providing conditions for activation, migration, dividing and proliferation of chondrocytes and for secretion of extracellular matrix ultimately leading to formation of the new hyaline cartilage and its integration into the native cartilage.

The method generally comprises steps:

a) fabrication of the acellular matrix implant according to the above described procedures;

b) debridement an articular cartilage lesion in surgical procedure;

c) during the debridement, preparing the lesion for implantation of the acellular matrix implant by depositing the bottom sealant at the bottom of the lesion thereby insulating said cavity from the surrounding tissue;

d) implanting the acellular matrix implant into said cavity formed by the polymerized bottom sealant to allow the activated and migrating chondrocytes to proliferate within said implant;

e) depositing the top sealant over the lesion, and thereby sealing said implant within the cavity formed between the two sealant layers;

f) optionally introducing enzymes, hormones, growth factors, proteins, peptides and other mediators into said sealed cavity by incorporating them into the acellular matrix, or coating said matrix with them, introducing them separately or generating conditions for their transport or transfer through the bottom sealant; and g) following the surgery, subjecting an individual undergoing a surgery for repair of said lesion to a normal physical activity thereby naturally providing an intermittent hydrostatic pressure which was shown to promote formation of the healthy hyaline cartilage and its integration into the surrounding native intact cartilage.

There are several advantages of the current method.

The main advantage of this method is that the acellular matrix implant is prepared beforehand and is implanted during the first and only surgery where the cleaning and debridement is immediately followed by implantation of the acellular matrix implant.

Second, the acellular implant avoids immunological reactions to develop as there is/are no foreign tissue or cells involved because the implant is wholly synthetic and acellular.

The method using the acellular matrix implant permits a three-dimensional expansion of chondrocytes and extracellular matrix.

The deposition of the top sealant layer resulting in formation of superficial cartilage layer constitutes a substitute for synovial membrane and provides the outer surface of healthy articular cartilage overgrowing, protecting, containing and providing critical metabolic factors aiding in protecting the implant and activated migrating chondrocytes in the lesion. The superficial cartilage layer also prevent invasion of pannus as seen in FIGS. 10A, 10B, 11A and 11B compared with FIGS. 8A, 8B, 9A and 9B, where the presence of the invading pannus is clearly visible. In some instances, a selection of the thermo-reversible gel may be crucial as certain TRGH may function as a promoter for growth of the superficial cartilage layer without a need to apply the top sealant.

Deposition of the bottom sealant layer protects the integrity of the lesion after cleaning during surgery and prevents migration of subchondral and synovial cells and cell products thereby creating milieu for formation of healthy hyaline cartilage from the activated migrating chondrocytes into the acellular matrix implant and also preventing formation of the fibrocartilage.

The method further permits said acellular matrix implant to be enhanced with hyaluronic acid or other components or mediators named above, typically added in about 5 to about 50%, preferably about 20% (v/v), wherein such hyaluronic acid or such other components act as enhancers of the matrix-forming characteristics of the gel and also as a hydration factor in the synovial space in general and within the lesion cavity in particular.

Further, the method is very versatile and any of the implant type variations may be advantageously utilized for treatment of a specific cartilage, osteochondral or bone injury, damage, aging or disease.

For treatment of the cartilage, a subject is treated, according to this invention, with a prepared acellular matrix implant implanted into the lesion, the implant is left in the lesion covered with the top sealant for as long as needed. Usually, during the two-three months following the surgery and implant implantation the new hyaline cartilage is formed and integrated into the native surrounding host cartilage. Typically also, there is no need for any further surgical or other intervention, as during these two-three months, at a normal physical activity, such as walking, running or biking, etc., a sufficient hydrostatic pressure is applied to the lesion to initiate and promote formation of the hyaline cartilage fully integrated into the native cartilage. Such cartilage will then become a fully functional cartilage covered with a superficial cartilage layer which eventually grows into or provides the same type of surface as a synovial membrane of the intact joint.

Finally, the method also permits replacement of the age worn-out or diseased osteoarthritic cartilage by the regenerated hyaline-like cartilage when treated according to this invention.

The implantation protocol may assume any variation described above or possible within the realm of this invention. It is thus intended that every and all variations in the treatment protocol, the types of the implants, use of one or two sealants, implantation process, selection of added mediators and not the least the normal physical activity of the individual are within the scope of the current invention.

VIII. Method for Treatment of Bone or Osteochondral Defects

The method for treatment of osteochondral defects is typically practiced in conjunction with treatment of cartilage. The method for treatment of bone defects and lesions may be practiced in conjunction with osteochondral defects or separately without steps involving deposition of the acellular implant into the cartilage.

A. Osteochondral Defects

Due to its anatomical arrangement where the subchondral bone is localized directly beneath the injured cartilage and the injury is both the injury to the cartilage and to the subchondral bone or subchondral skeletal bone, the method for treatment of osteochondral defects is an extension of the method for treatment of cartilage lesions described in section VII, with exception that during the step c) of that method, the surgeon, after debridement, deposits into the subchondral bone lesion a bone-inducing composition or a carrier comprising said composition typically comprising one or several bone-inducing agent (s), as described above, then covers said composition with a layer of the bottom sealant, and after permitting the sealant or the composition or both to polymerize, performs the steps a–g. The nature of this type of defects is such that as a consequence of the thinness of the subchondral bone layer there is high probability that the lesion will extend into the underlying cancellous bone. In such an instance, the bone-inducing composition or bone acellular implant is deposited into the skeletal bone and in flowable continuation into the osteochondral bone which is then covered with the bottom sealant layer and the acellular implant is deposited as described above.

B. Bone Defects

The true bone defects, lesions or fractures are stand alone injuries in the skeletal bone. These types of injuries may also be conveniently treated according to the invention with the bone-inducing composition or with a carrier comprising such bone-inducing composition.

The carrier, in this setting, corresponds to the acellular implant utilized for treatment of bone. This bone acellular implant comprises bone-inducing agents.

The treatment of the skeletal bone injuries comprises depositing of the bone-inducing composition into the lesion or fracture during the surgery. Typically, the bone-inducing composition will be administered directly into the lesion or fracture as a powder or a solution, such as an adhesive or polymerizable solution, or the composition will be incorporated into a bone-inducing carrier or porous matrix as described above. The bone lesion may or may not then be covered with the top sealant or any other surface to contain the composition within the lesion.

In the preferred embodiment, the demineralized bone powder is used as a powder or in solution wherein said powder is dissolved in the collagen, hydrogel or some other adhesive solution which has no bone forming effect. The bone-inducing composition is added in amount which will completely fill the lesion or fracture.

IX. Treatment of Human Osteoarthritic Cartilage

Articular cartilage is a unique tissue with no vascular, nerve, or lymphatic supply. The lack of vascular and lymphatic circulation may be one of the reasons why articular cartilage has such a poor intrinsic capacity to heal, except for formation of fibrous or fibrocartilaginous tissue. Unique mechanical functions of articular cartilage are never reestablished spontaneously after a significant injury, age wear or disease, such as osteoarthritis (OA).

Currently, the only available treatment of severe osteoarthritis of the knee is a total knee replacement in elderly patients. In young and middle aged patients, however, this is not an optimal treatment.

Although the current invention is more practicable for treatment of injuries in young individuals who naturally possess sufficient levels of extracellular matrix building enzymes, growth factors, and other mediators, the method may be advantageously modified to also provide treatment for older population.

For treatment of elderly patients or for treatment of larger lesions, the acellular matrix implant is incorporated, before implantation, with one or more metalloproteinases, mediators, enzymes and proteins and/or with drugs stimulating endogenous production of these factors and mediators. These factors, as described above, stimulate and promote chondrocytes activation, migration and extracellular matrix secretion. The method of the invention thus is also suitable for treatment of the cartilage defects in older generation. It is expected, however, that such treatment will require longer period of treatment.

In osteoarthritis, or in age worn out cartilage, disruption of the structural integrity of the matrix by the degeneration of individual matrix proteins leads to reduced mechanical properties and impaired function. Consequently, the current invention reverses this process by providing a means for rebuilding the diseased osteoarthritic or worn cartilage with the new healthy hyaline cartilage.

X. In vivo Studies in Swine of the Weight-Bearing Region of the Knee

The method according to the invention was tested and confirmed in in vivo studies in swine.

The studies, described below, were designed to evaluate feasibility of the porcine acellular matrix implant by detecting chondrocyte activation and induction of chondrocyte migration on the surrounding cartilage, generation of newly synthesized hyaline cartilage within the lesion and formation of superficial cartilage layer.

Studies involved the creation of defects in the weight-bearing region of the femoral medial condyle of the knee joint, implantation of the acellular matrix into the defect, depositing bottom and top sealants, detection of growth of a superficial cartilage layer after two weeks following the defect creation, detection of chondrocyte morphology, detection of pannus invasion and presence of fibrocartilage, detection of presence or absence of S-GAG secretion, histochemical evaluation of presence or absence of sealants.

Figure 3:
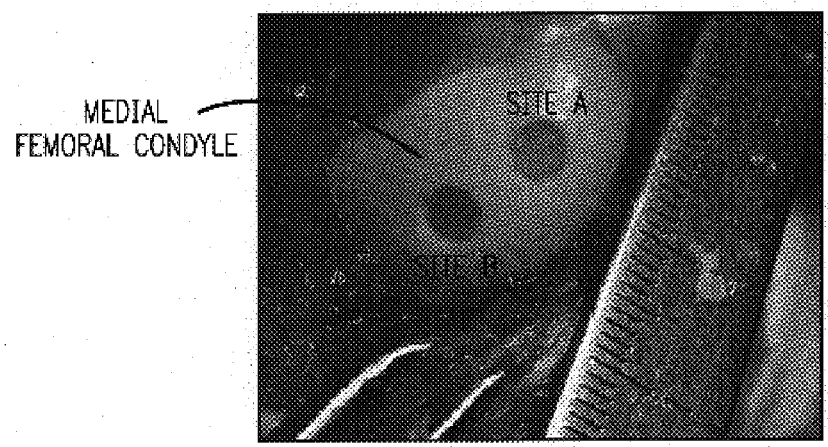
FIG. 3 shows a micrograph of the two control empty defect sites A and B (4 mm in diameter and 1–1.5 mm in depth) created on the weight-bearing site of the swine medial femoral condyle.
Figure 4:
FIG. 4 is a micrograph of the two defect sites A and B generated on the weight-bearing site of the swine medial femoral condyle, implanted with acellular matrix implants. The defect has 4 mm in diameter and 1–1.5 mm in depth. The implants have 5 mm diameter and 1.5 mm thickness. Each implant is sutured using 4 absorbable sutures and two non-absorbable sutures. The defect was lined up with the bottom sealant and the implant was covered with the top sealant.

Gross anatomy of the empty defect creation and acellular matrix implantation at day zero is shown in FIGS. 3 and 4. Formation of the healthy hyaline cartilage and generation of the superficial cartilage layer in defects treated with the acellular matrix implant and the fibrocartilage pannus invasion in control defects at seven month following the defect creation are seen in FIGS. 5–12.

FIG. 3 shows two empty defects sites A and B at a time of the defect creation (time zero). FIG. 4 shows two defects created at time zero implanted with the acellular matrix implants at sites A and B.

Figure 5:
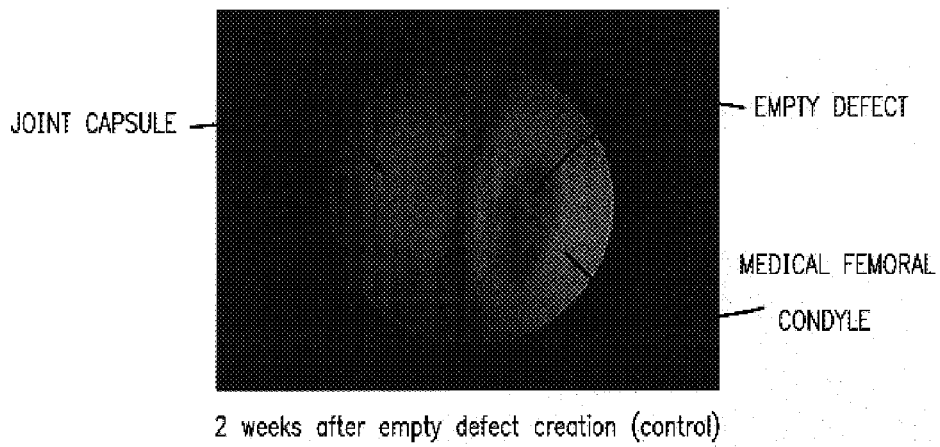
FIG. 5 shows arthroscopic evaluation of a magnified empty defect 2 weeks after defect creation showing the defect to be fully exposed and empty.
Figure 6:
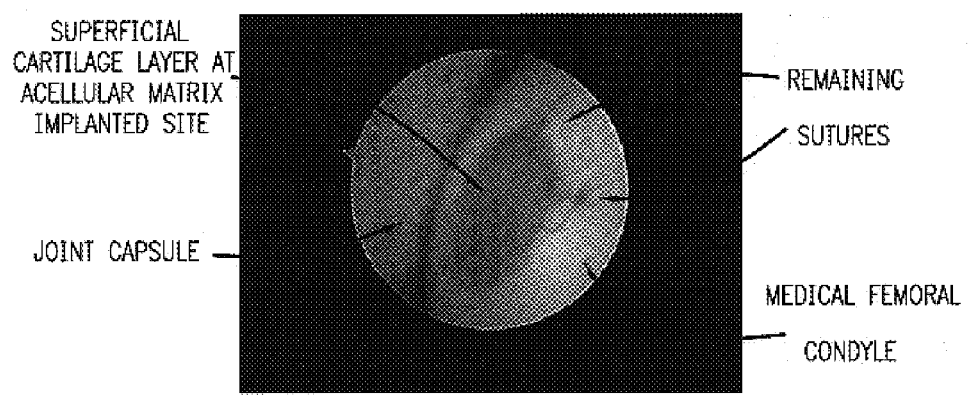
FIG. 6 shows arthroscopic evaluation of a magnified defect treated with the acellular matrix implant 2 weeks after the defect creation. The superficial cartilage layer overgrowing the implant site forms a smooth flat surface over the defect.
Figure 7:
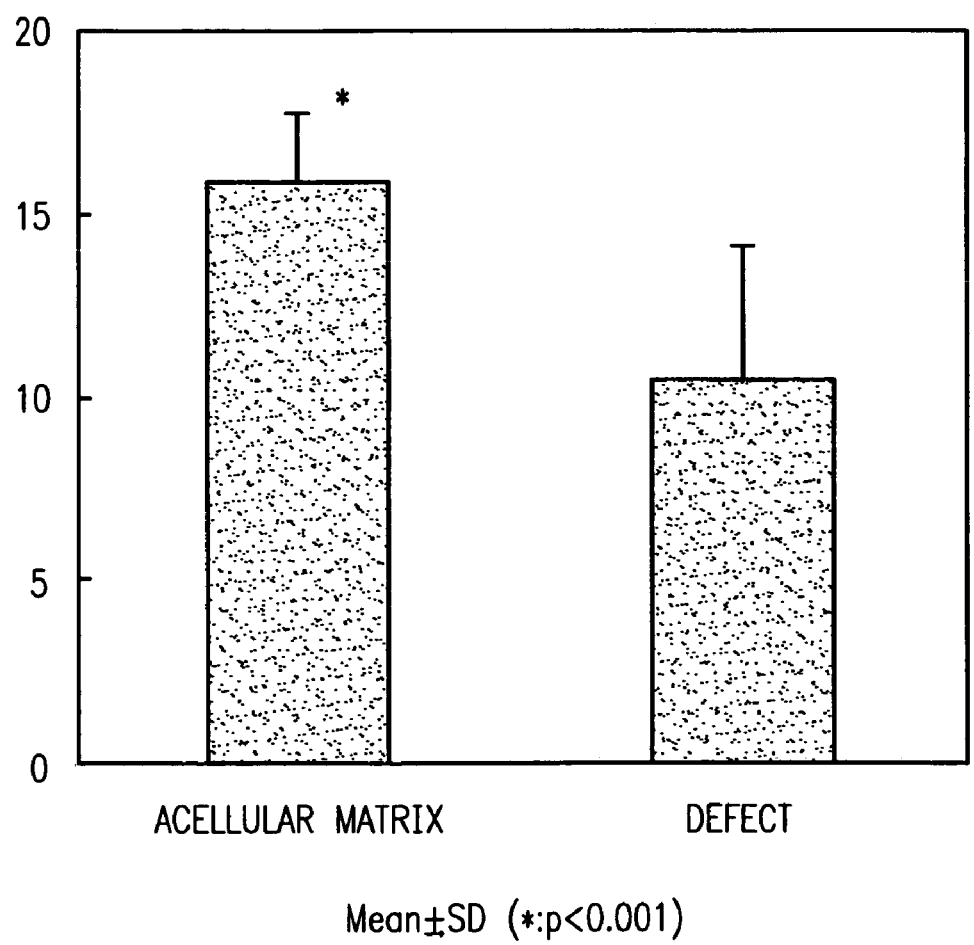
FIG. 7 is a graph illustrating a histological grading of the repair tissue.
Figure 12A:
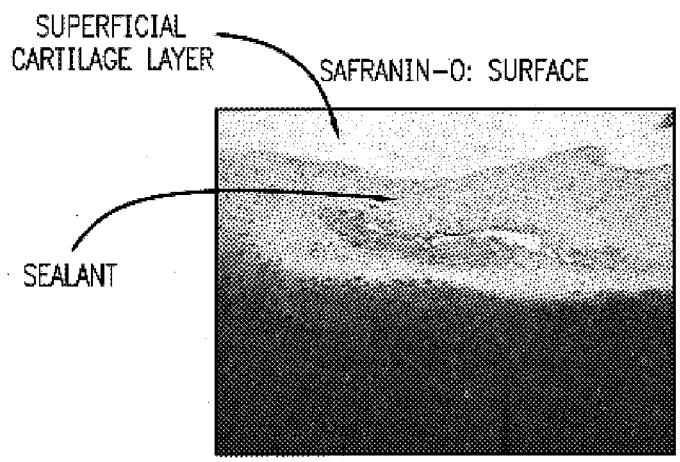
FIG. 12A shows a surface view of the Safranin-O stained implantation site.
Figure 12B:
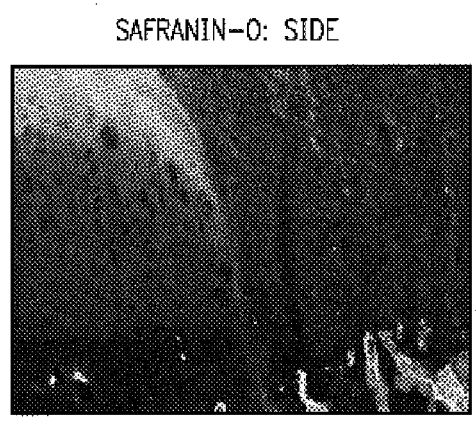
FIG. 12B shows a side view of the Safranin-O stained implantation site.
Figure 12C:
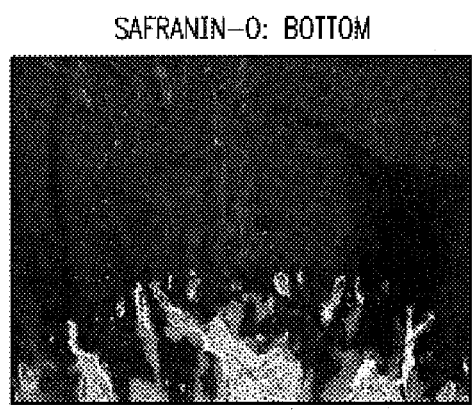
FIG. 12C shows the bottom view of the Safranin-O stained implantation site. Safranin-O staining, seen as reddish color, indicates S-GAG accumulation.
Figure 13:
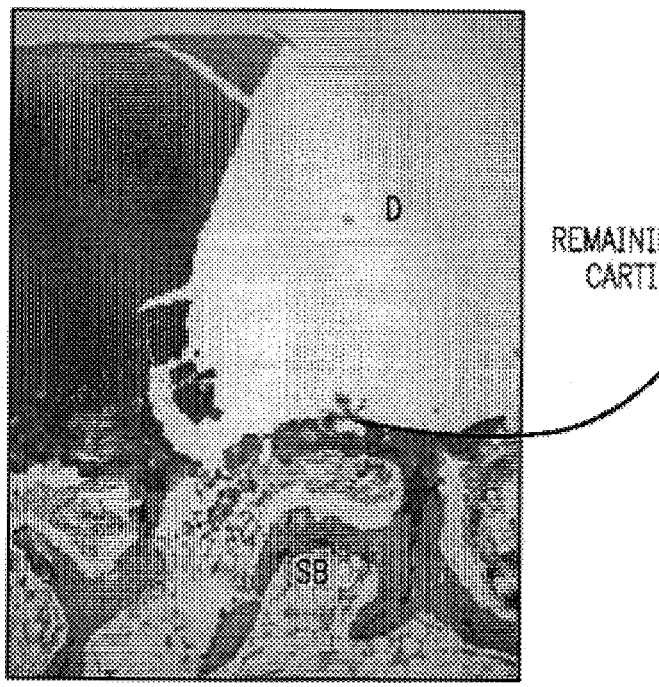
FIG. 13 shows an example image of a full thickness defect (D) after harvest created at femoral condyle of mini-pig at 72× magnification. Surrounding host cartilage (H), subchondral bone area (SB) and remaining calcified cartilage area are also indicated.

FIGS. 5 and 6 show arthroscopic evaluation two weeks after defect creation in the control group (FIG. 5) and in the experimental group implanted with the acellular matrix (FIG. 6). Histological grading is seen in FIG. 7 and histological evaluation, in two magnifications, is seen in FIGS. 8 and 9 for the control animals and in FIGS. 10 and 11 for the experimental group treated with the acellular implant. Degradation of the sealant from the cartilage lesion is seen in FIGS. 12A–12C. One example of full thickness defect at femoral condyle of mini-pig is seen in FIG. 13.

Figure 1D:
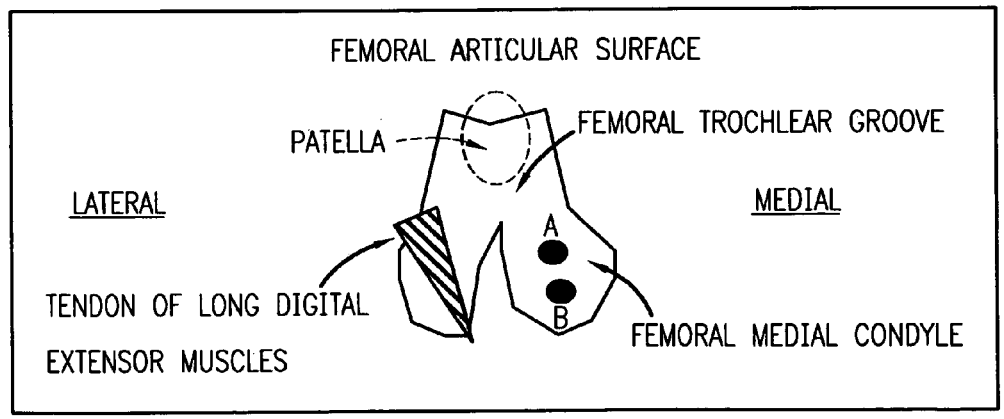
FIG. 1D is a schematic depiction of creation of defects A and B at weight bearing site for implantation of an acellular matrix implant or serving as an empty control defect.

Schematic representation of the femoral articular surface, defect creation and implant implantation sites within said defect is shown in FIG. 1D. FIG. 1D shows two defects A and B created in the femoral medial condyle on the medial side of the femoral articular surface. The defects have sizes of 4 mm in diameter and 1–1.5 mm in depth. The defects are created in the weight-bearing region.

Table 1 is a tabulation of conditions of a study design as schematically illustrated in FIG. 1D.

TABLE 1

Study Design

| Group Number | Number of Animals | Number of Samples | Procedure | Arthroscopy | Necropsy |
|---|---|---|---|---|---|
| 1 Experimental | 8 | 16** | Implantation of acellular biodegradable matrix* | 2 weeks after implantation | 7 months after implantation |
| 2 Control | 8 | 16** | Empty defect control | 2 weeks after defect creation | 7 months after defect creation |

*Matrix was secured with tissue adhesive and sutures.
**Each group has two samples at weight-bearing site (site A and B, FIG. 1D).

Table 1 illustrates the study design for the seven months study of feasability of the acellular matrix implant for treatment of cartilage lesions. Study involved 8 castrated male Yucatan micro-swine, 9–12 months old in each of the two groups. Two defects (A and B) were created at time zero in the knee of each animal, with a total number of 16 defects. The experimental group was implanted with acellular matrix implant at a time of defect creation. In the control group, the defect was left empty without any treatment and was used for visual, microscopical, histological and histochemical comparisons. Arthroscopy was performed at 2 weeks after implantation and defect creation. Necropsy was performed 7 months after implantation and defect creation.

The acellular matrix implant was prepared from a collagen solution VITROGEN® (35 μL) obtained from Cohesion, Calif. The collagen gel solution was absorbed into a collagen honeycomb sponge (5 mm in diameter and 1.5 mm in thickness) obtained from Koken Co., Japan. The combined collagen gel/sponge constructs seen in FIG. 2A were pre-incubated for 1 hour at 37° C. to gel the collagen, followed by incubation in culture medium with 1% penicillin and streptomycin at 37° C. at 5% $CO_2$. After about 24 hours of polymerization, the biodegradable scaffolds were transferred to the tissue container with pre-warmed culture medium (37° C.) for the implantation.

Arthrotomy was performed under an inhalation anesthesia. After opening knee joint capsule, two empty full-thickness defects (4 mm in diameter and about 1.5 mm in depth) were created in the femoral articular cartilage on the weight-bearing site of the medial femoral condyle of each animal. After creating defects, tissue sealant was placed on the bottom of the defect. Then, the pre-prepared acellular biodegradable matrix was placed over the bottom sealant within the cartilage lesion. The acellular matrix was secured with absorbable sutures (usually 4 to 6 sutures) and with two non-absorbable sutures. The non-absorbable sutures were used as a maker for arthroscopic evaluation and are visible in FIG. 6. The implanted defect was then sealed with the top sealant. For the controls, two empty full-thickness defects were created and left intact, that is empty, without implants, or deposition of the bottom or top sealants.

FIG. 3 shows a photograph of the two empty full-thickness defects A and B (4 mm in diameter and 1–1.5 mm in depth) created in the articular cartilage on the weight-bearing site of the medial femoral condyle. The empty defects were left intact during the whole time of the study and were used as controls for the experimental group.

FIG. 4 is a photograph of the two full-thickness defects created in the same way as the empty defects seen in FIG. 3. These two defects were treated, according to the method of the invention, with the bottom sealant deposited on the bottom of the lesion. The acellular matrix implant was implanted into the lesion cavity over the bottom sealant and the top sealant deposited the over the implanted acellular matrix implant. The implants were collagenous sponges (FIG. 2A) and had 5 mm in diameter and 1.5 mm in thickness. Both sites A and B were implanted. Each implant was secured with four absorbable sutures and two non-absorbable sutures used as markers for future arthroscopic evaluation.

Two weeks after defect creation and acellular matrix implantation, the empty defects and implant sites were evaluated with arthroscopy. Arthroscopic evaluation after 2 weeks is seen in FIGS. 5 and 6.

FIG. 5 is an arthroscopic microphotograph of an empty defect 2 weeks after defect creation. Arthroscopic evaluation showed that in the control group, if left untreated, the lesion was invaded with synovial pannus and filled with fibrocartilage. The arthroscopic evaluation clearly shows the defect depression indicating that the defect is fully exposed and empty although some synovial invasion have already occurred. Such synovial invasion is a first step toward formation of fibrocartilage. Formation of fibrocartilage to replace the hyaline cartilage is undesirable as the fibrocartilage is qualitatively and functionally inferior to hyaline cartilage.

Arthroscopic evaluation of implanted sites showed that already at two weeks time the defects are covered with the superficial cartilage layer. FIG. 6 is an arthroscopic microphotograph of the defect treated with the acellular matrix implant 2 weeks after the defect was created. The FIG. 6 shows the superficial cartilage layer overgrowing the implant site forming a smooth flat surface. The borders of the implant site are already undefined compared to the empty defect which has a definite and visible border, said implanted site indicating the beginning of chondrocyte migration into the implant and secretion of extracellular matrix in confluency with the host cartilage, all this covered with the superficial cartilage layer. The arthroscopic evaluation seen in FIG. 6 revealed that the lesion implanted with the acellular matrix is unexposed and covered with the superficial cartilage layer completely overgrowing the implant sites, seen as a smooth flat surface when compared to the fully exposed and empty defects of controls, seen in FIG. 5.

At 7 months after creating the defects and implanting the acellular matrix implants, the animals were euthanized. The implant and defect sites on the femoral articular condyle were harvested for histological evaluation. The tissues were fixed with 4% formaldehyde/PBS for 7 days at 4° C. The tissues were decalcified with 10% formic acid, processed, and embedded in paraffin. Thin sections (5 μm) were stained with Safranin-O (Saf-O) and hematoxylin eosin (H-E) for histological evaluation.

The stained sections were evaluated blindly by means of a histological grading scale seen in FIG. 7, modified from *J. Bone Joint Surg. Am.*, 79:1452–63 (1997). Only sections from the center of the defect were graded in order to ensure unbiased analysis and to allow comparison among specimens studied at different time-point. The area from the center of the defect was also chosen because it provided the most stringent test of healing capacity, since the least amount of cartilage healing was found consistently in specimens taken from the middle of the defect.

Histological scoring system used for cartilage repair evaluation is seen in Table 2.

TABLE 2

| Category |
| --- |
| 1. Filling of defect |

| Score | Filling of Defect |
| --- | --- |
| 0 | None (or almost none) |
| 1 | <50% |
| 2 | >50% |
| 3 | All (or almost all) |

| 2. Integration of repair tissue with surrounding articular cartilage |
| --- |

| Score | Integration |
| --- | --- |
| 0 | Gap or lack of continuity on two sides |
| 1 | Gap or lack of continuity on one sides |
| 2 | Non-continuous gap or lack |
| 3 | Normal continuity and integration |

TABLE 2-continued

| Category |
| --- |
| 3. Matrix staining with Safranin O-fast green (compared to host cartilage) |

| Score | Matrix staining |
| --- | --- |
| 0 | None (or almost none) |
| 1 | Slight |
| 2 | Moderate |
| 3 | All (or almost all) |

| 4. Cellular morphology |
| --- |

| Score | Chondrocytes morphology |
| --- | --- |
| 0 | Mostly spindle-shape (fibrous-like) cells |
| 1 | <50% of round cells with morphology of chondrocytes |
| 2 | >50% of round cells with morphology of chondrocytes |
| 3 | Normal (mostly round cells with morphology of chondrocytes) |

| 5. Architecture within entire defect (not including margins) |
| --- |

| Score | Architecture within entire defect |
| --- | --- |
| 0 | Clefts or fibrillations |
| 1 | <3 large voids |
| 2 | >3 large voids |
| 3 | Normal |

| 6. Architecture of surface |
| --- |

| Score | Architecture of surface |
| --- | --- |
| 0 | Severe fibrillation or irregularity |
| 1 | Moderate fibrillation or irregularity |
| 2 | Slight fibrillation or irregularity |
| 3 | Normal (or nearly normal) |

| 7. Penetration of tissue to subchondral bone area |
| --- |

| Score | Penetration |
| --- | --- |
| 0 | Severe penetration |
| 1 | Moderate penetration |
| 2 | Slight penetration |
| 3 | Normal (or nearly normal) |

Cumulative results of the histological grading of the repaired chondral cartilage is seen in Table 3.

TABLE 3

Histological Grading of the Repaired Cartilage

| Category | Acellular Matrix Group | Empty Defect Group |
| --- | --- | --- |
| Filling of defect | 3.00 | 2.60 |
| Integration | 2.00 | 1.40 |
| Matrix staining | 2.33 | 2.10 |
| Chondrocyte morphology | 1.78 | 0.80 |
| Architecture within entire defect | 2.33 | 0.30 |
| Architecture of surface | 2.33 | 1.90 |
| Tissue penetration into subchondral bone area | 2.11 | 1.40 |
| Average total score | 15.88 | 10.50 |
| SD± | 1.90 | 3.60 |

As seen in Table 3 the average total score for histological grading at 7 months after the defect creating and treatment with the acellular matrix implant was much higher in the implant group, with the score for all indicators in the implant group being higher then in the empty defect group.

Histological grading of the repair tissue is shown in FIG. 7, which graphically illustrates results shown in Table 5. The average total scores on the histological grading scale were significantly better (p<0.001) for the defects treated with acellular matrix implants than for the untreated defects.

At seven months following the defect creation, animals were sacrificed, their joints were harvested and evaluated by Safranin-O staining. Results are seen in FIGS. 8–11.

The non-implanted, empty defects A and B at 7 months after defect creating are shown in FIGS. 8A, 8B, 9A and 9B.

Figure 8A:
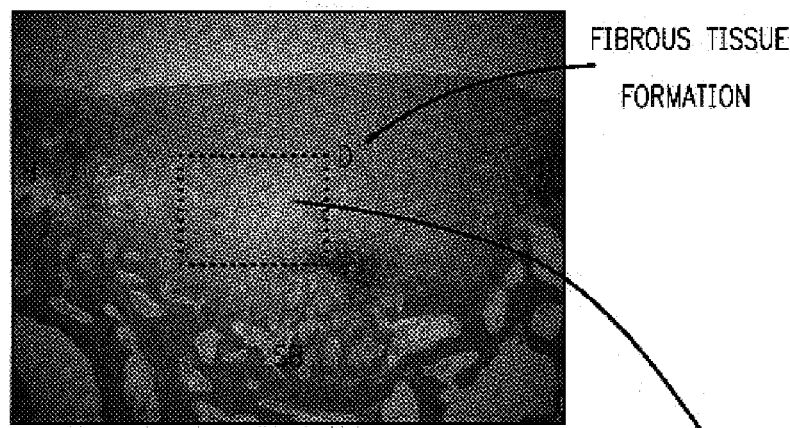
FIG. 8A shows a histological evaluation (29× magnification) of the empty defect (D) at a control site (A).
Figure 8B:
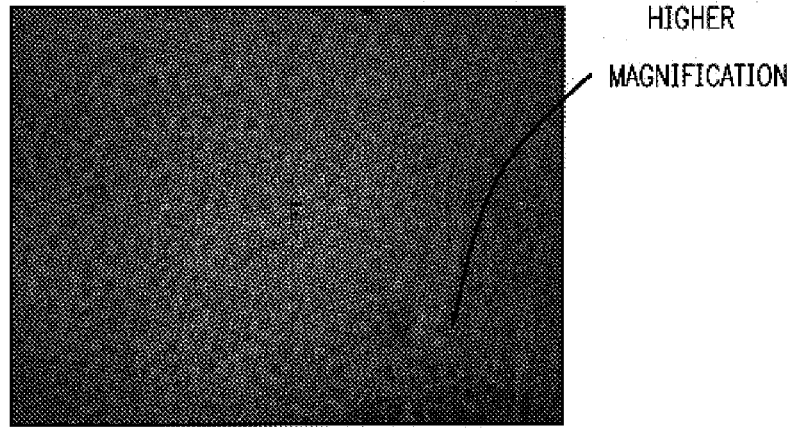
FIG. 8B shows a higher (72×) magnification of the defect site (D). The defect is surrounded by the host cartilage (H) with underlying subchondral bone (SB) area. Fibrous tissue (F) formation is seen in both figures at the empty defect site. Fibrovascular pannus (F) is formed at empty defect site as indicated by the absence of the S-GAG accumulation.

FIG. 8A is a Safranin-O staining microphotograph (29× magnification) of the empty, non-implanted defect (D) at a control site A seven months after defect creation. In higher magnification (FIG. 8B), the defect clearly shows a fibrous tissue (F) filling the defect surrounded by the host cartilage (H) with underlying subchondral bone (SB) area (FIG. 8A). None or a very small amount of S-GAG accumulation, depicted by red color, was observed at the defect site. S-GAG accumulation is evidence of the extracellular matrix formation. If there is a little or none S-GAG present, there is no extracellular matrix generated, indicating the absence of migrating chondrocytes and absence of formation of hyaline cartilage. It also indicates the presence and formation of fibrocartilage within the lesion. FIG. 8B shows a 72× magnification of the defect site confirming a presence of fibroblasts, that is fibrous cells, indicating invasion of a fibrovascular pannus (F) from synovium. Chondrocyte morphology showed presence of mostly spindle (fibrous) cells.

Figure 9A:
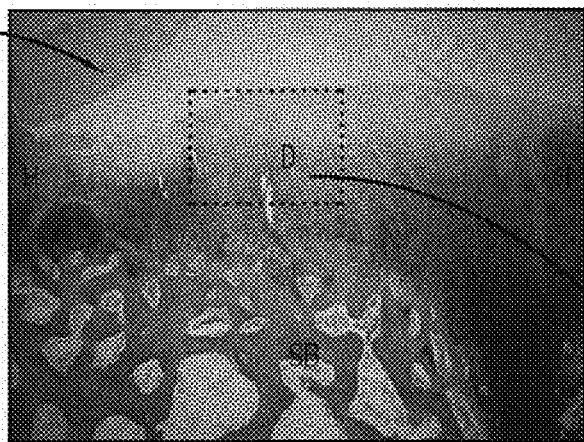
FIG. 9A shows a histological evaluation (29× magnification) of the empty defect (D) at a control site (B).

FIG. 9A is a Safranin-O staining microphotograph (29× magnification) of the empty, non-implanted defect (D) at a site B of the control defect seven months after defect creation showing a formation of fibrous tissue filling the defect surrounded by the host cartilage (H) with underlying subchondral bone (SB) area. Severe irregularity of the lesion surface was observed. Only very slight S-GAG accumulation, depicted by red color, was observed at the defect site. S-GAG accumulation is evidence of the extracellular matrix formation.

Figure 9B:
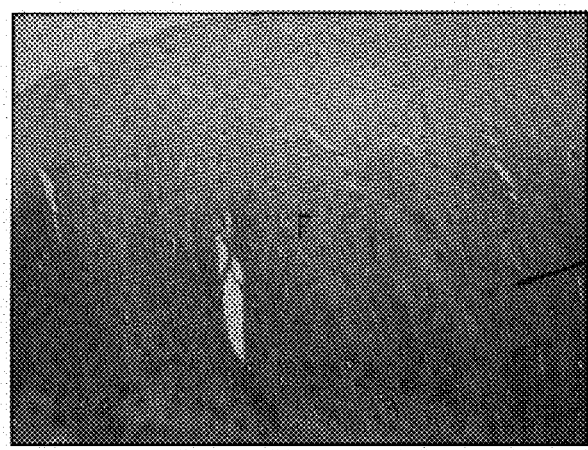
FIG. 9B shows a higher (72×) magnification of the defect site (D). The defect is surrounded by the host cartilage (H) with underlying subchondral bone (SB) area. Fibrous tissue (F) formation is seen in both FIGS. 9A and 9B at the empty defect site with slight accumulation of S-GAG accumulation.

FIG. 9B shows a 72× magnification of the defect site showing a presence of fibroblasts indicating a fibrovascular pannus (F) invasion from synovium. Cell morphology observed at this site shows mostly spindle fibrous cells.

FIGS. 8A, 8B, 9A and 9B clearly show that non-implanted control defects without treatment with the acellular implant of the invention do not indicate a formation of the healthy hyaline cartilage which would show as S-GAG accumulation, in Safranin-O stained microphotograps seen as a red color. Rather, these microphotographs show fibrovascular pannus synovial invasion into the defect with an accumulation of spindly fibrous cells present in the empty defect sites.

While the no-treatment of the lesion resulted in the filing of the defect with the fibrocartilage, the implantation of the acellular matrix implant into the defect induced chondrocyte activation and migration from the surrounding native cartilage and resulted in massive formation of cartilage extracellular matrix (ECM accumulation) with minimal fibrovascular pannus in the implant sites. ECM accumulation was detected by the strong red color present at the implanted sites of experimental animals. Results are seen in FIGS. 10A, 10B, 11A and 11B.

Figure 10A:
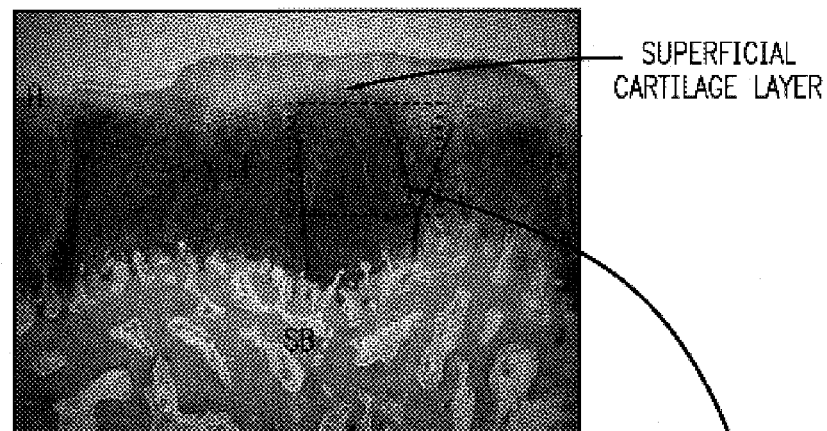
FIG. 10A shows a histological evaluation (29× magnification) of the acellular implantation (I) at the implant site (A).

FIG. 10A is a micrograph of Safranin-O staining histological evaluation (29× magnification) of the acellular matrix implant (I) implanted withing the defect site A, seven month after defect creation and implantation of the acellular matrix implant. FIG. 10A clearly shows induction of cell migration from the surrounding native host cartilage (H) into the implant (I) implanted within the defect site. After seven months following the implantation, hyaline-like cartilage was observed at the acellular implant site. The presence of the hyaline cartilage is indicated by the normal S-GAG accumulation, seen as a predominant red present in the defect site A. Superficial cartilage layer formed over the lesion is also seen. There was minimal fibrovascular pannus in the implant sites. Implant is surrounded by the host cartilage (H) with underlying subchondral bone area (SB).

Figure 10B:
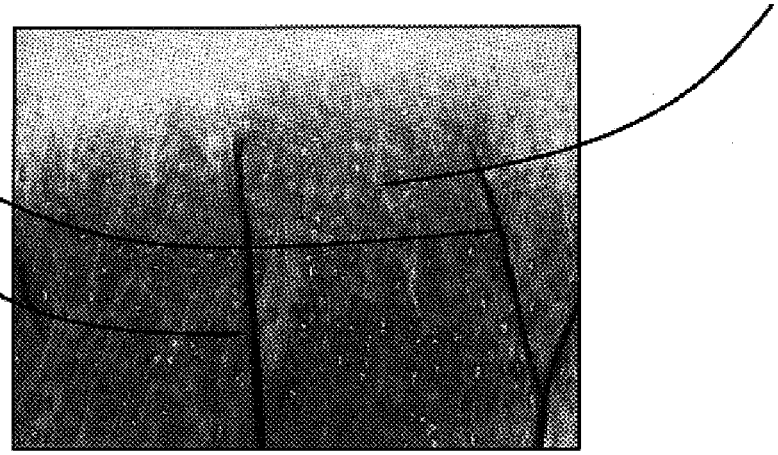
FIG. 10B shows acellular implantation at higher (72×) magnification of the implant site (I). The implant site is surrounded by the host cartilage (H) with underlying subchondral bone (SB) area. Superficial cartilage layer is shown to cover the implant site. In both FIGS. 10A and 10B normal S-GAG accumulation and formation of hyaline-like cartilage was observed at the implant site.

FIG. 10B shows a higher magnification (72×) of the implant area with red color indicative of S-GAG accumulation and chondrocyte morphology showing primarily normal mostly round cells as compared to spindly fibrous cells observed in the non-treated control defects.

Figure 11A:
FIG. 11A shows a histological evaluation (29× magnification) of the acellular implantation (I) at the implant site (B).

FIG. 11A is a Safranin-O staining histological evaluation (29× magnification) of the acellular matrix implant (I) implanted withing the defect site B, seven month after implantation. FIG. 11A confirms results seen in FIG. 10A. It clearly shows induction of cell migration from the surrounding native host cartilage (H) into the implant (I) implanted within the defect site. At seven months after implantation, hyaline-like cartilage was observed at the acellular implant site. The presence of the hyaline cartilage was indicated by the normal S-GAG accumulation, seen as a predominant red color present in the defect site B. Superficial cartilage layer formed over the lesion and traces of non-absorbable suture are also seen. No fibrovascular pannus synovial invasion was observed in the implant site. Implant is surrounded by the host cartilage (H) with underlying subchondral bone area (SB). The non-absorbable suture indicates the original border between the host cartilage and the implant, now almost completely obscured.

Figure 11B:
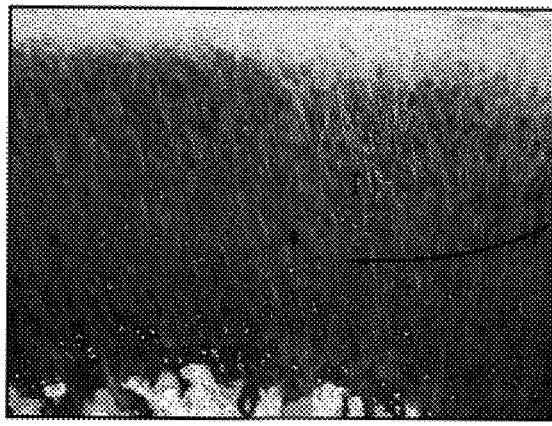
FIG. 11B shows acellular implantation at higher (72×) magnification of the implant site (I). The implant site is surrounded by the host cartilage (H) with underlying subchondral bone (SB) area. Superficial cartilage layer is shown to cover the implant site. In both FIGS. 11A and 11B normal S-GAG (*) accumulation and formation of hyaline-like cartilage was observed at the implant site.

FIG. 11B shows a higher magnification (72×) of the implant area with high accumulation of red color indicative of S-GAG presence. Chondrocyte morphology again show primarily normal, mostly round cells confirming results observed at site A.

As seen in FIGS. 10A and 10B, 11A and 11B, there was clearly visible integration between the biodegradable acellular matrix and the host cartilage. Such integration is not observed in FIGS. 8A and 9A where the defect is surrounded by the normal hyaline cartilage. These figures show different cell morphology at the defect sites than those at the implantation sites seen in FIGS. 10A and 10B. Cell morphology of the empty sites shows the presence of spindly fibrous cells dissimilar to those cells of the surrounding hyaline cartilage. Cell morphology at the implanted sites, on the other hand, show the presence of the normal (round) cells also observed in the surrounding healthy hyaline cartilage. The implanted site thus, after seven months does not show difference between the previously uninjured cartilage and the one formed within the defect following the implantation.

Additionally, the use of a top sealant deposited over the implant implanted at a defect site had resulted in formation of the superficial cartilage layer and minimizing synovial tissue invasion at the implant site.

A superficial cartilage layer is formed over the cartilage lesion after the top sealant is deposited over the lesion implanted with the acellular implant. As seen in FIG. 6, the presence of the superficial cartilage layer was already observed in two weeks after the implantation. The top sealant which causes the superficial cartilage layer to be formed is biodegradable and biodegrades within the time. At three months after the sealant deposition, remaining sealant was still observed at the surface area along with the superficial cartilage layer. At seven months after implantation, the top sealant was completely biodegraded and superficial cartilage layer was formed in its place, as seen in FIGS. 10A and 11A.

In order to determine the sealant (top and bottom) degradation in vivo, articular cartilage samples implanted with an autologous chondrocyte construct using the scaffold matrix were stained with Safranin-O (FIGS. 12A–12C). Reddish color in Safranin-O stained figures indicates S-GAG accumulation. Purple color indicates remaining tissue adhesive with amorphous structure.

FIG. 12 thus illustrates a degradation pattern, in time, of the top and bottom sealants three months after the acellular matrix implantation. At that time, the superficial cartilage layer was formed over the implant and the top sealant was partially degraded. The bottom sealant was, at three months following its deposition at the bottom of the lesion, completely degraded and removed from the lesion site.

FIG. 12A shows a surface view of the Safranin-O stained implantation site with the superficial cartilage layer clearly visible and the small amount of the top sealant remaining under the superficial cartilage layer. FIG. 12B shows a side view of the Safranin-O stained implantation site. FIG. 12C shows the bottom view of the Safranin-O stained implantation site where at time zero the bottom sealant was deposited.

In this test, the remaining top sealant was observed only at the surface between the top of the regenerated hyaline like cartilage region and superficial cartilage layer (FIG. 12A). There was no indication in side view of any remaining top or bottom sealant between the interface of the implant site and the surrounding host cartilage (FIG. 12B). There was no remaining bottom sealant at the bottom of the lesion interfacing with the subchondral bone region where the bottom sealant was deposited at time zero (FIG. 12C).

These results indicate that the bottom sealant is completely biodegraded and removed from the lesion site in about three month after implantation. At that time, there are still remnants of the top sealant visible on the surface of the lesion where the sealant protects the acellular implant from any migration or invasion of synovium and at the same time supports the formation of the superficial cartilage layer. With time even these remnants of the top sealant are biodegraded and removed from the healed lesion as evidenced by a complete absence of any top or bottom sealant at the defect site.

A reason why the top sealant is still present at three months time is that, compared to the surface area, the side and bottom of the acellular implant site are more active regions for cell migration which is important for cell integration and formation of hyaline cartilage. In these regions, the sealant was completely degraded within 3 months. This phenomenon occurred and was observed in both the cellular and acellular matrix implantation in vivo. Cellular implant is described in copending application Ser. No. 10/625,245 filed on Jul. 22, 2003.

In order to confirm that the surgical technique used for creation of the cartilage defects in control and experimental animals is distinguished from the microfracture technique which penetrates the subchondral bone area, an image of full thickness defect at femoral condyle of mini-pig was created and is shown, with 72× magnification, in FIG. 13. FIG. 13 shows a paraffin embedded and Safranin-O stained reference tissue of the created full thickness defect. The defect was created of non-treated articular cartilage and bone from the femoral condyle surrounded by the host cartilage and underlying subchondral bone area. The remaining calcified cartilage area is seen in the area above the subchondral bone. This tissue was utilized in all studies as a reference tissue used for histological evaluation.

The results described above show that implantation of the biodegradable acellular matrix implant into the cartilage lesion according to the invention induces chondrocyte migration from surrounding native cartilage and formation of an extracellular matrix and leads to synthesis of a new hyaline cartilage with minimal synovial invasion of fibrovascular pannus at the implant sites.

Synthesis of the new hyaline cartilage was measured by the extracellular matrix accumulation expressed as accumulation of S-GAG. Also observed was a cell integration between the biodegradable acellular implant and the host cartilage. The use of a bottom and top sealants and sutures primarily to secure the implant within the defect suggest that these could have a secondary effect of minimizing synovial tissue invasion at the implant site. On the other hand, the results described above and illustrated by the figures clearly show that the intact nontreated control defects result in synovial invasion of the defect with fibrovascular pannus.

The acellular matrix implant most suitable for practicing the invention comprises a porous honeycomb sponge of Type I atelocollagen filled with a thermoreversing hydrogel of Type I collagen sandwiched between a bottom layer and a top layer of the sealant. The type I collagen cell walls of the porous honeycomb add further strength to the sealing capacity of the sealant by adding to the collagen-PEG chemical interaction analogously to the reaction of metal reinforcing bar to concrete.

The acellular implant itself is fully biodegradable in time. During that time the following conditions are observed in sexually mature but not fully epiphysealy-fused mini-swine. It is observed that in a 2 mm lesion of the femoral condyle covered with the top sealant, a superficial cartilage layer extending from the edge of the healthy cartilage region peripheral to the acellular implant proceeds to overgrow the lesion and the sealant layer. Additionally, chondrocyte migration into the acellular implant and production of the new hyaline cartilage matrix that eventually fills and replaces the implant is observed. This new cartilage matrix is or closely resembles hyaline cartilage as measured by sulfated glycoaminoglycan content and histological appearance. The source of these migrating chondrocytes are likely to be both the peripheral deeper layers of healthy chondrocytes peripheral to the acellular implant, and also the overgrown superficial cartilage layer, since it is shown that this layer is the source of differentiated chondrocytes capable of producing hyaline cartilage. Eventually hyaline-like cartilage is found to fill the implant while at the same time the implanted acellular matrix is gradually biodegraded.

In the current methodological arrangement, the top and bottom sealants is intended to prevent debris from subchondral space to enter the implant (bottom sealant) and to sequester the implant within a lesion space (top sealant). The acellular matrix implant sequestered within the lesion permits chondrocytes from the surrounding healthy cartilage to migrate and enter the matrix. Naturally applied hydrostatic pressure during a normal physical activity promotes chondrogenesis leading to a formation of true hyaline cartilage and to a healing of the lesion.

Results of studies described above confirm that the damaged, injured, diseased or aged cartilage may be repaired by using acellular implants prepared according to the invention and that the acellular matrix implant of the invention induces cell migration from surrounding healthy host cartilage and its implantation induces the inward growth of the superficial cartilage membrane from the healthy tissue on the periphery. This membrane, superficial cartilage layer, protects the implant within the lesion from any synovial invasion. Once the implant is properly implanted within the lesion, the natural physicochemical factors, such as intermittent hydrostatic pressure, low oxygen tension and growth factors induce the cartilage recovery.

The advantages of the acellular matrix implant system are multiple. There is no need for biopsy and cell harvesting, no need to cover periosteum over the lesion, no damage to healthy tissue, the second and third surgery is eliminated resulting in faster recovery and elimination of waiting periods for the next surgery.

Advantages listed above are similarly attached to treatments of subchondral or bone lesions.

EXAMPLE 1

Preparation of Acellular Collagenous Implants

This example illustrates preparation of the acellular matrix implant.

300 grams of a 1% aqueous atelocollagen solution (VITROGEN®), maintained at pH 3.0, is poured into a 10×20 cm tray. This tray is then placed in a 5 liter container. A 50 ml open container containing 30 ml of a 3% aqueous ammonia solution is then placed next to the tray, in the 5 liter chamber, containing 300 grams of said 1% aqueous solution of atelocollagen. The 5 liter container containing the open trays of atelocollagen and ammonia is then sealed and left to stand at room temperature for 12 hours. During this period the ammonia gas, released from the open container of aqueous ammonia and confined within the sealed 5 liter container, is reacted with the aqueous atelocollagen resulting in gelling said aqueous solution of atelocollagen.

The collagenous gel is then washed with water overnight and, subsequently, freeze-dried to yield a sponge like matrix. This freeze dried matrix is then cut into squares, sterilized, and stored under a sterile wrap.

Alternatively, the support matrix may be prepared as follows.

A porous collagen matrix, having a thickness of about 4 mm to 10 mm, is hydrated using a humidity-controlled chamber, with a relative humidity of 80% at 25° C, for 60 minutes. The collagen material is compressed between two Teflon sheets to a thickness of less than 0.2 mm. The compressed material is then cross-linked in a solution of 0.5% formaldehyde, 1% sodium bicarbonate at pH 8 for 60 minutes. The cross-linked membrane is then rinsed thoroughly with water, and freeze-dried for about 48 hours. The dense collagen barrier has an inner implantation of densely packed fibers that are intertwined into a multi-layer structure.

In alternative, the integration layer is prepared from collagen-based dispersions or solutions that are air dried into sheet form. Drying is performed at temperatures ranging from approximately 4 to 40° C. for a period of time of about 7 to 48 hours.

For histological evaluation, 4% paraformaldehyde-fixed, paraffin sections were stained with Safranin-O (Saf-O) and Type II collagen antibody.

For biochemical analysis, seeded sponges were digested in papain at 60° C. for 18 hours and DNA content was measured using the Hoechst 33258 dye method. Sulfated glycosaminoglycan (S-GAG) accumulation was measured using a modified dimethylmethylene blue (DMB) microassay.

EXAMPLE 2

Biochemical and Histological Assays

This example describes assays used for biochemical and histological studies.

For biochemical (DMB) assay, the implant taken from the animal after certain time following the implantation, transferred to microcentrifuge tubes and digested in 300 µl of papain (125 µg/ml in 0.1 M sodium phosphate, 5 mM disodium EDTA, and 5 mM L-cysteine-HCl) for 18 hours at 60° C. S-GAG production in the implant is measured using a modified dimethylene blue (DMB) microassay with shark chondroitin sulfate as a control according to *Connective Tissue Research*, 9: 247–248 (1982).

DNA content is determined by Hoechst 33258 dye method according to *Anal. Biochem.*, 174:168–176 (1988).

For histological assay, the remaining implants from each group were fixed in 4% paraformaldehyde. The implants were processed and embedded in paraffin. 10 µm sections were cut on a microtome and stained with Safranin-O (Saf O).

For immunohistochemistry, the samples are contacted with diaminobenzidine (DAB). The DAB is a color substrate showing brown color when the reaction is positive.

EXAMPLE 3

Evaluation of Integration of Acellular Matrix Implant in a Swine Model

This example describe the procedure and results of study performed for evaluation of integration of porcine in a swine model.

An open arthrotomy of the right knee joint was performed on all animals, and a biopsy of the cartilage was obtained.

A defect was created in the medial femoral condyle of the pig's right knee. This defect (control) was not implanted with an acellular matrix implant but was left intact. Following surgery, the joint was immobilized with an external fixation implant for a period of about two weeks. Two weeks after the arthrotomy on the right knee was performed, an open arthrotomy was performed on the left knee and defects were created in this medial femoral condyle. The acellular matrix implant was implanted within the defect(s) in this knee which was similarly immobilized. The operated sites were subsequently viewed via arthroscopy two weeks after implantation or defect creation and thereafter at monthly intervals.

Animals were euthanized and the joints harvested and prepared for histological examination approximately 7 months after acellular matrix implant implantation. The implanted sites were prepared and examined histological.

What is claimed:

1. A method for treatment of injury of an articular cartilage and for repair and restoration of damaged, injured, diseased or aged cartilage to a functional hyaline cartilage, said method comprising steps:

a) preparing a three-dimesional acellular matrix implant wherein said acellular matrix implant is a sponge, porous scaffold, honeycomb scaffold, honeycomb lattice, gel, sol-gel or thermo-reversible hydrogel, said implant prepared from a material selected from the group consisting of a Type I collagen, a Type II collagen, a Type IV collagen, a polymer of an aromatic organic acid or a copolymer thereof, gelatin, a bioactive peptide, a growth factor, cytokine, polycaprolactone, polyamino acid, a gel, a sol-gel, a hydrogel, a thermo-reversible gelling hydrogel (TRGH), a copolymer thereof and a combination thereof;
b) depositing a layer of a biologically acceptable bottom sealant rapidly gelling for from 30 second to about 15 minutes from a flowable liquid or paste to a load-bearing gel over a bottom of an articular cartilage lesion to protect the lesion cavity from blood-borne agents, migrating cells and cell debris;
c) implanting said implant into an articular cartilage lesion cavity in situ;
d) depositing a layer of a biologically acceptable top sealant to seal the lesion cavity wherein said top sealant seals the implant within said cavity, protects the implant and promotes a formation of a superficial cartilage layer; and wherein said top or bottom sealant is selected from the group consisting of gelatin and di-aldehyde starch mixture, 4-armed pentaerythritol tetra-thiol and polyethylene mixture, polyethylene glycol-co-poly(α-hydroxy acid) diacrylate, a mixture of a copolymer of polyethylene glycol with polylactide, polyglycolide, polyhydroxybutyrate or a polymer of aromatic organic acid, polyethylene glycol derivatized with succinimidyl ester or thiol, a cross-linked polyethylene glycol with collagen, and a cross-linked polyethylene glycol with methyl collagen.

2. The method of claim 1 wherein said top or bottom sealant is the cross-linked polyethylene glycol with methyl collagen.

3. The method of claim 1 wherein said gelling time of the top or bottom sealant is from 3 to 5 minutes.

4. The method of claim 1 wherein said top or bottom sealant has an adhesive bonding peel strength between 10 N/m to 100 N/m and cohesive strength between 0.2 to 1.0 MPa.

5. The method of claim 1 wherein said acellular matrix implant comprises a combination of a sponge, porous scaffold, honeycomb scaffold or a honeycomb lattice with a gel, a polypeptide gel, sol-gel, a thermo-reversible gelling hydrogel (TRGH), a polymer of an aromatic organic acid or a copolymer thereof.

6. The method of claim 2 suitable for treatment of the articular cartilage injury comprising steps:
a) preparation of the acellular matrix implant;
b) debridement of said lesion during the surgery;
c) preparation of the cartilage lesion for implantation of said implant, including a step of depositing the bottom sealant at the bottom of the cartilage lesion for sealing of said lesion and protecting the implant from migration of blood-borne agents, subchondral or synovial cells or cell debris;
d) implanting the implant into the lesion;
e) depositing the top sealant over the acellular matrix implant; and
f) following the surgery, subjecting an individual undergoing a surgery for repair of said lesion to a normal physical activity.

7. The method of claim 6 wherein said acellular matrix implant is a biodegradable collagenous sponge, honeycomb sponge, collagenous porous scaffold, a polymer of an aromatic organic acid, a thermo-reversible gelation hydrogel (TRGH) or a combination thereof.

8. The method of claim 7 wherein said matrix implant or said bottom sealant additionally comprises matrix remodeling enzymes, matrix metalloproteinases, aggrecanases and cathepsins or wherein said enzymes, metalloproteinases, aggrecanases and cathepsins are added to the lesion cavity.

9. The method of claim 1 additionally comprising a step of debridement of the articular cartilage lesion.

10. The method of claim 9 further comprising a step of optionally introducing enzymes, hormones, growth factors, proteins, peptides, mediators, or drugs promoting an endogenous production of these factors or mediators, into said sealed cavity, adding them to the bottom sealant, or generating conditions for their transport or transfer through the bottom sealant.

11. The method of claim 9 further comprising a step of subjecting an individual undergoing a surgery for repair of said lesion to a normal physical activity.

* * * * *